US008671118B2

(12) United States Patent
Kanada

(10) Patent No.: US 8,671,118 B2
(45) Date of Patent: Mar. 11, 2014

(54) APPARATUS, METHOD AND PROGRAM FOR ASSISTING MEDICAL REPORT CREATION AND PROVIDING MEDICAL INFORMATION

(75) Inventor: Shoji Kanada, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 140 days.

(21) Appl. No.: 13/216,640

(22) Filed: Aug. 24, 2011

(65) Prior Publication Data
US 2012/0054230 A1  Mar. 1, 2012

(30) Foreign Application Priority Data

Aug. 25, 2010  (JP) ................................. 2010-188689
Aug. 25, 2010  (JP) ................................. 2010-188690
Aug. 31, 2010  (JP) ................................. 2010-195104

(51) Int. Cl.
G06F 17/30  (2006.01)
(52) U.S. Cl.
USPC ........... 707/803; 707/759; 707/769; 707/809; 707/812
(58) Field of Classification Search
USPC ........................ 707/759, 769, 803, 809, 812
See application file for complete search history.

(56) References Cited

U.S. PATENT DOCUMENTS

| 8,249,732 | B2* | 8/2012 | Stephens et al. | ................. | 700/98 |
| 2005/0010859 | A1* | 1/2005 | McDonough et al. | ........ | 715/500 |
| 2006/0248480 | A1* | 11/2006 | Faraday et al. | ............... | 715/866 |
| 2007/0237377 | A1* | 10/2007 | Oosawa | ......... | 382/128 |
| 2009/0249192 | A1* | 10/2009 | Chan et al. | .................... | 715/235 |
| 2009/0279760 | A1* | 11/2009 | Bergman | ...................... | 382/128 |
| 2009/0287559 | A1* | 11/2009 | Chen et al. | ................. | 705/14.23 |
| 2010/0114597 | A1* | 5/2010 | Shreiber et al. | ................... | 705/2 |
| 2010/0138239 | A1* | 6/2010 | Reicher et al. | .................... | 705/3 |

FOREIGN PATENT DOCUMENTS

| JP | 06-292656 | 10/1994 |
| JP | 2001-118012 | 4/2001 |
| JP | 2002-203045 | 7/2002 |
| JP | 2004-252615 | 9/2004 |
| JP | 2005-510326 | 4/2005 |
| JP | 2008-176596 | 7/2006 |
| JP | 2007-018460 | 1/2007 |

(Continued)

OTHER PUBLICATIONS

JP Office Action dated Oct. 1, 2013, with English translation; Application No. 2010-195104.

(Continued)

Primary Examiner — Mohammad S Rostami
(74) Attorney, Agent, or Firm — Young & Thompson

(57) ABSTRACT

On a medical report editing screen, comments on a lesion are entered as selective input data through a lesion describing template having term selection buttons. The selective input data are stored in a database in association with a lesion ID given to each lesion. To describe another similar lesion in the same report, a copy of the previous template is displayed as an additional tab reproducing the same condition as the previous template. By searching using the selective input data or the lesion ID, data of past medical reports on the same lesion are retrieved from the database. Using the retrieved data, information on the course of this lesion is displayed. A template describing the same lesion in the past medical report is usable for describing the lesion in the present report, and the selective input data of the present report is stored with the same lesion ID used previously.

19 Claims, 33 Drawing Sheets

(56) References Cited

FOREIGN PATENT DOCUMENTS

| | | |
|---|---|---|
| JP | 2007-122679 | 5/2007 |
| JP | 2008-009589 | 1/2008 |
| JP | 2008-027099 | 2/2008 |
| JP | 2008-146220 | 6/2008 |
| JP | 2009-080731 | 4/2009 |
| JP | 2009-082442 | 4/2009 |
| JP | 2009-271620 | 11/2009 |
| JP | 2009-271621 | 11/2009 |

OTHER PUBLICATIONS

JP Office Action dated Oct. 9, 2013, with English translation; Application No. 2010-188690.

Japanese Official Action—2010-188689—Nov. 13, 2013.

* cited by examiner

FIG.4

| | | | | | |
|---|---|---|---|---|---|
| HEPATIC MORPHOLOGY | TUMOR MASS LESION | CALCIFICATION | OVERALL LIVER — 50 | | |

| | | ENTRY | | NEW COPY ▽ | ADD LESION — 63 |
|---|---|---|---|---|---|
| | SITE | | S2 | | |
| | SIZE | 30 mm X | 20 mm | | |
| | NUMBER | SINGLE | DISSEMINATED | MULTIPLE | |
| | SHAPE | OVAL | IRREGULAR | MASSIVE | SPREAD PARTS |
| | INTERNAL ECHO | ANECHOIC | HYPOECHOIC | ISOECHOIC | HYPERECHOIC | MIXED ECHOIC |
| | ECHO PATTERN | SOLID | MIXED | CYSTIC | | |
| | HOMOGENEITY | HOMOGENOUS | HETEROGENEOUS | | | |
| | BORDER | CLEAR | UNCLEAR | | | |
| | MARGIN | NO ECHO ZONE | HYPOECHOIC ZONE | HYPERECHOIC ZONE | | |
| | POSTERIOR ECHO | ATTENUATED | UNCHANGED | ENHANCED | SLIGHTLY ENHANCED | NULL |
| | BLOODSTREAM SIGNAL | NO | FEW | MANY | | |
| | CALCIFICATION | NO | YES | | | |
| | INTRAHEPATIC BILE DUCT DILATION | NO | YES | | | |
| INFILTRATION | PRESENCE | | YES | | | |
| | INFILTRATED PART | INFILTRATED PART | | | | |

60, 61, 62, 51, 52

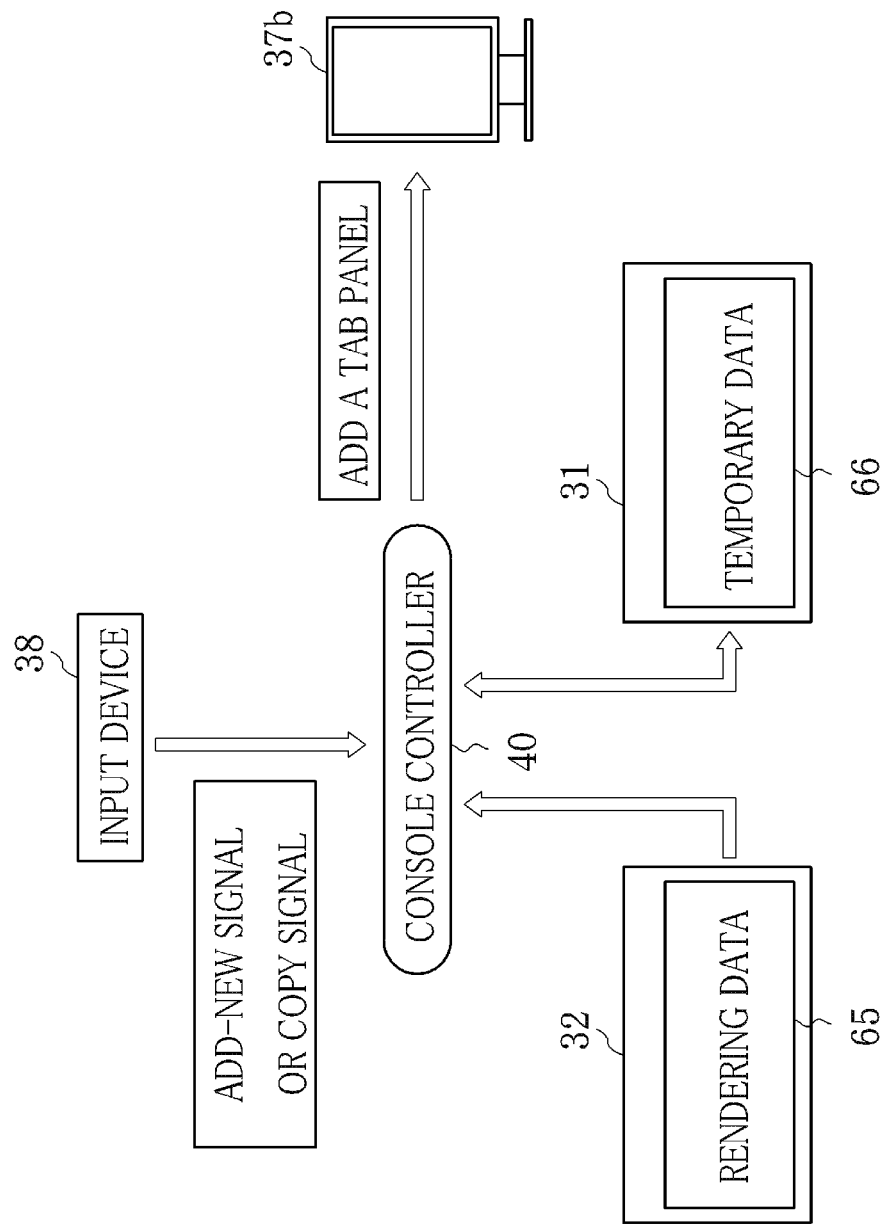

FIG.6

| | HEPATIC MORPHOLOGY | TUMOR MASS LESION | #2 | CALCIFICATION | OVERALL LIVER |
|---|---|---|---|---|---|
| | | | | ENTRY | NEW ▽ | ADD LESION | DELETE |
| | SITE | | | | | |
| | SIZE | mm × mm | | | | |
| | NUMBER | SINGLE | DISSEMINATED | MULTIPLE | | PARTS |
| | SHAPE | OVAL | IRREGULAR | MASSIVE | SPREAD | |
| | INTERNAL ECHO | ANECHOIC | HYPOECHOIC | ISOECHOIC | HYPERECHOIC | MIXED ECHOIC |
| | ECHO PATTERN | SOLID | MIXED | CYSTIC | | |
| | HOMOGENEITY | HOMOGENOUS | HETEROGENEOUS | | | |
| | BORDER | CLEAR | UNCLEAR | | | |
| | MARGIN | NO ECHOIC ZONE | HYPOECHOIC ZONE | HYPERECHOIC ZONE | | |
| | POSTERIOR ECHO | ATTENUATED | UNCHANGED | ENHANCED | SLIGHTLY ENHANCED | NULL |
| | BLOODSTREAM SIGNAL | NO | FEW | MANY | | |
| | CALCIFICATION | NO | YES | | | |
| | INTRAHEPATIC BILE DUCT DILATION | NO | YES | | | |
| INFILTRATION | PRESENCE | | | | | |
| | INFILTRATED PART | INFILTRATED PART | | | | |

FIG.7

| HEPATIC MORPHOLOGY | TUMOR MASS LESION | #2 | CALCIFICATION | OVERALL LIVER |

| | | ENTRY | | | |
|---|---|---|---|---|---|
| | SITE | | | | |
| | SIZE | mm × | mm | | |
| | NUMBER | SINGLE | DISSEMINATED | MULTIPLE | |
| | SHAPE | OVAL | IRREGULAR | MASSIVE | PARTS |
| | INTERNAL ECHO | ANECHOIC | HYPOECHOIC | ISOECHOIC | HYPERECHOIC | MIXED ECHOIC |
| | ECHO PATTERN | SOLID | MIXED | CYSTIC | SPREAD |
| | HOMOGENEITY | HOMOGENOUS | HETEROGENEOUS | | |
| | BORDER | CLEAR | UNCLEAR | | |
| | MARGIN | NO ECHO ZONE | HYPOECHOIC ZONE | HYPERECHOIC ZONE | |
| | POSTERIOR ECHO | ATTENUATED | UNCHANGED | ENHANCED | SLIGHTLY ENHANCED | NULL |
| | BLOODSTREAM SIGNAL | NO | FEW | MANY | |
| | CALCIFICATION | YES | NO | | |
| | INTRAHEPATIC BILE DUCT DILATION | YES | NO | | |
| INFILTRATION | PRESENCE | NO | | | |
| | INFILTRATED PART | INFILTRATED PART | | | |

| | | | | | |
|---|---|---|---|---|---|
| HEPATIC MORPHOLOGY | TUMOR MASS LESION | #2 | CALCIFICATION | OVERALL LIVER | |

COURSE INFORMATION — 78
80 — ADD
69 — #2
50 — OVERALL LIVER
62 — COPY ▽
63 — ADD LESION
64 — DELETE
61
52
51

| | | | | | |
|---|---|---|---|---|---|
| SITE | | ENTRY | | | |
| SIZE | | mm X | mm | | |
| NUMBER | | SINGLE | MULTIPLE | | |
| SHAPE | | OVAL | DISSEMINATED | MASSIVE | |
| | | | IRREGULAR | | |
| INTERNAL ECHO | | ANECHOIC | HYPOECHOIC | ISOECHOIC | HYPERECHOIC | MIXED ECHOIC |
| ECHO PATTERN | | SOLID | MIXED | CYSTIC | SPREAD | PARTS |
| HOMOGENEITY | | HOMOGENOUS | HETEROGENEOUS | | | |
| BORDER | | CLEAR | UNCLEAR | | | |
| MARGIN | | NO ECHOIC ZONE | HYPOECHOIC ZONE | HYPERECHOIC ZONE | | |
| POSTERIOR ECHO | | ATTENUATED | UNCHANGED | ENHANCED | SLIGHTLY ENHANCED | NULL |
| BLOODSTREAM SIGNAL | | NO | NO | FEW | MANY | |
| CALCIFICATION | | NO | YES | | | |
| INTRAHEPATIC BILE DUCT DILATION | | NO | YES | | | |
| INFILTRATION | PRESENCE | | | | | |
| | INFILTRATED PART | INFILTRATED PART | | | | |

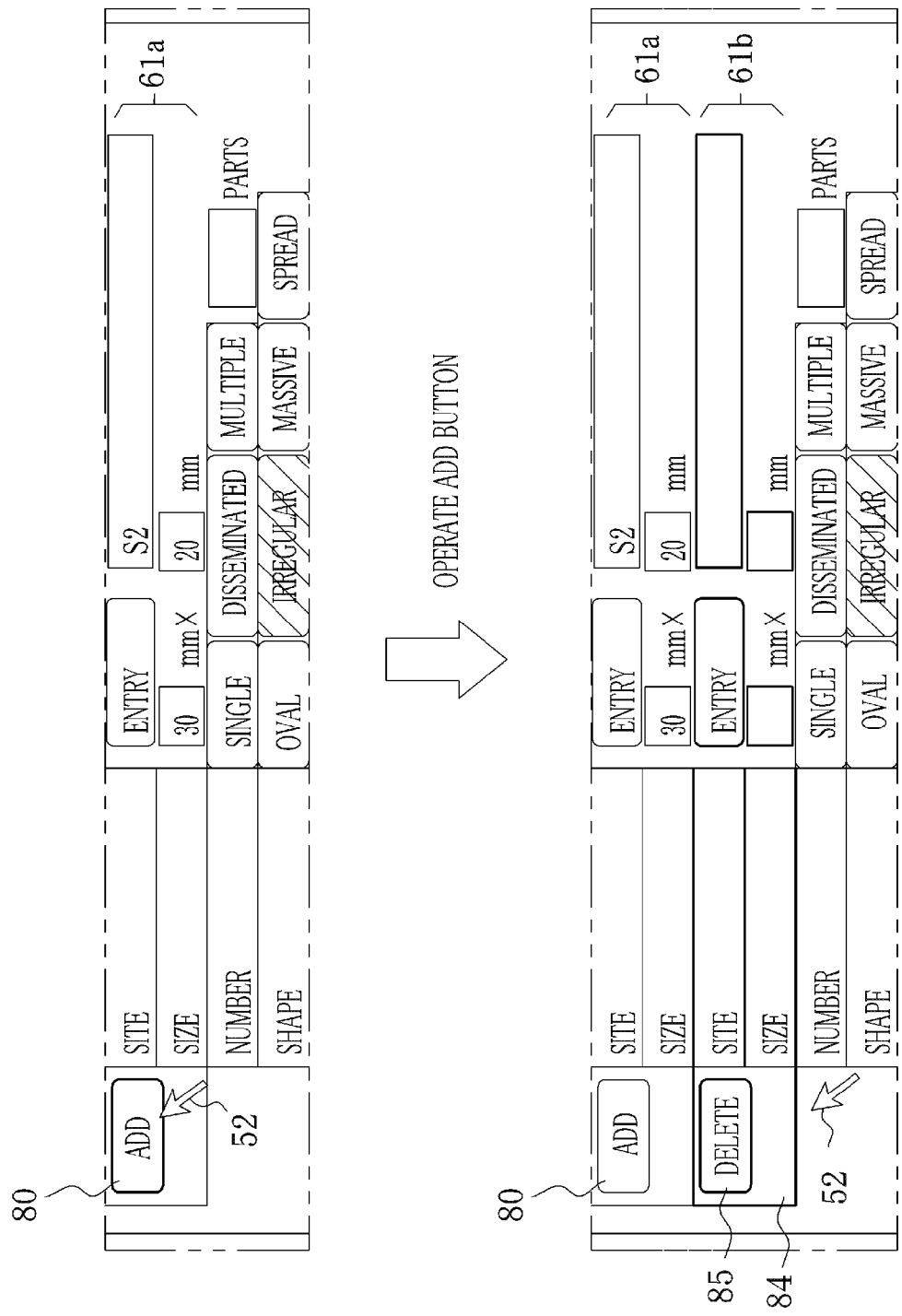

FIG.18

| PATIENT ID | LESION ID | CONDITION OF SELECTIVE INPUT | DIAGNOSTIC NAME | COURSE | STAGE | REPORT ID | DATE OF EXAMINATION | ... |
|---|---|---|---|---|---|---|---|---|
| 01234 | 00001 | SITE: S2, SIZE: 30mm, 20mm NUMBER: NO SELECTION SHAPE: IRREGULAR INTERVAL ECHO: HYPOECHOIC··· | MALIGNANCY | | TYPE I | 01524 | 10/7/30 | |
| | | SITE: S2 SIZE: 34mm, 25mm··· | MALIGNANCY | WORSE | TYPE I | 01545 | 10/8/3 | |
| | | SITE: S2 SIZE: 22mm, 15mm··· | MALIGNANCY | BETTER | TYPE I | 01572 | 10/8/6 | |
| | | SITE: S2 SIZE: 22mm, 15mm··· | MALIGNANCY | UNCHANGED | TYPE I | 01596 | 10/8/14 | |
| | | ... | | | | | | |
| | 00002 | SITE: PUTAMEN VOLUME: 3.5cc GREATEST DIMENSION: 23mm··· | CEREBRAL HEMORRHAGE | | | 01680 | 10/9/1 | |
| | | SITE: PUTAMEN VOLUME: 0.5cc GREATEST DIMENSION: 12mm··· | CEREBRAL HEMORRHAGE | BETTER | | 01692 | 10/9/4 | |
| | | SITE: PUTAMEN VOLUME: 0cc GREATEST DIMENSION: 0mm··· | CEREBRAL HEMORRHAGE | DISAPPEAR | | 01715 | 10/9/11 | |
| | 00003 | SITE: CEREBELLUM VOLUME: 3.4cc GREATEST DIMENSION: 23mm··· | CEREBRAL HEMORRHAGE | | | 01680 | 10/9/1 | |
| | | SITE: CEREBELLUM VOLUME: 1.8cc GREATEST DIMENSION: 12mm··· | CEREBRAL HEMORRHAGE | BETTER | | 01692 | 10/9/4 | |
| | | SITE: CEREBELLUM VOLUME: 1.7cc GREATEST DIMENSION: 12mm··· | CEREBRAL HEMORRHAGE | UNCHANGED | | 01715 | 10/9/11 | |
| 01284 | 00062 | SIZE: 3cm CALCIFICATION: YES··· | AORTIC ANEURYSM | | | 01528 | 10/8/1 | |
| | ... | ... | | | | | | |

| PATIENT ID | LESION ID | DATE OF EXAMINATION | SITE | SIZE | DIAGNOSTIC NAME | COURSE | STAGE |
|---|---|---|---|---|---|---|---|
| 01234 | 00001 | 10/7/30 | S2 | 30mm×20mm | MALIGNANCY | | TYPE I |
| | | 10/8/3 | S2 | 34mm×25mm | MALIGNANCY | WORSE | TYPE I |
| | | 10/8/6 | S2 | 22mm×15mm | MALIGNANCY | BETTER | TYPE I |
| | | 10/8/14 | S2 | 22mm×15mm | MALIGNANCY | UNCHANGED | TYPE I |

| PATIENT ID | LESION ID | DATE OF EXAMINATION | SITE | VOLUME | GREATEST DIMENSION | DIAGNOSTIC NAME | COURSE |
|---|---|---|---|---|---|---|---|
| 01234 | 00002 | 10/9/1 | PUTAMEN | 3.5cc | 23mm | CEREBRAL HEMORRHAGE | |
| | | 10/9/4 | PUTAMEN | 0.5cc | 12mm | CEREBRAL HEMORRHAGE | BETTER |
| | | 10/9/11 | PUTAMEN | 0cc | 0mm | CEREBRAL HEMORRHAGE | DISAPPEAR |
| | 00003 | 10/9/1 | CEREBELLUM | 3.4cc | 23mm | CEREBRAL HEMORRHAGE | |
| | | 10/9/4 | CEREBELLUM | 1.8cc | 12mm | CEREBRAL HEMORRHAGE | BETTER |
| | | 10/9/11 | CEREBELLUM | 1.7cc | 12mm | CEREBRAL HEMORRHAGE | UNCHANGED |

88

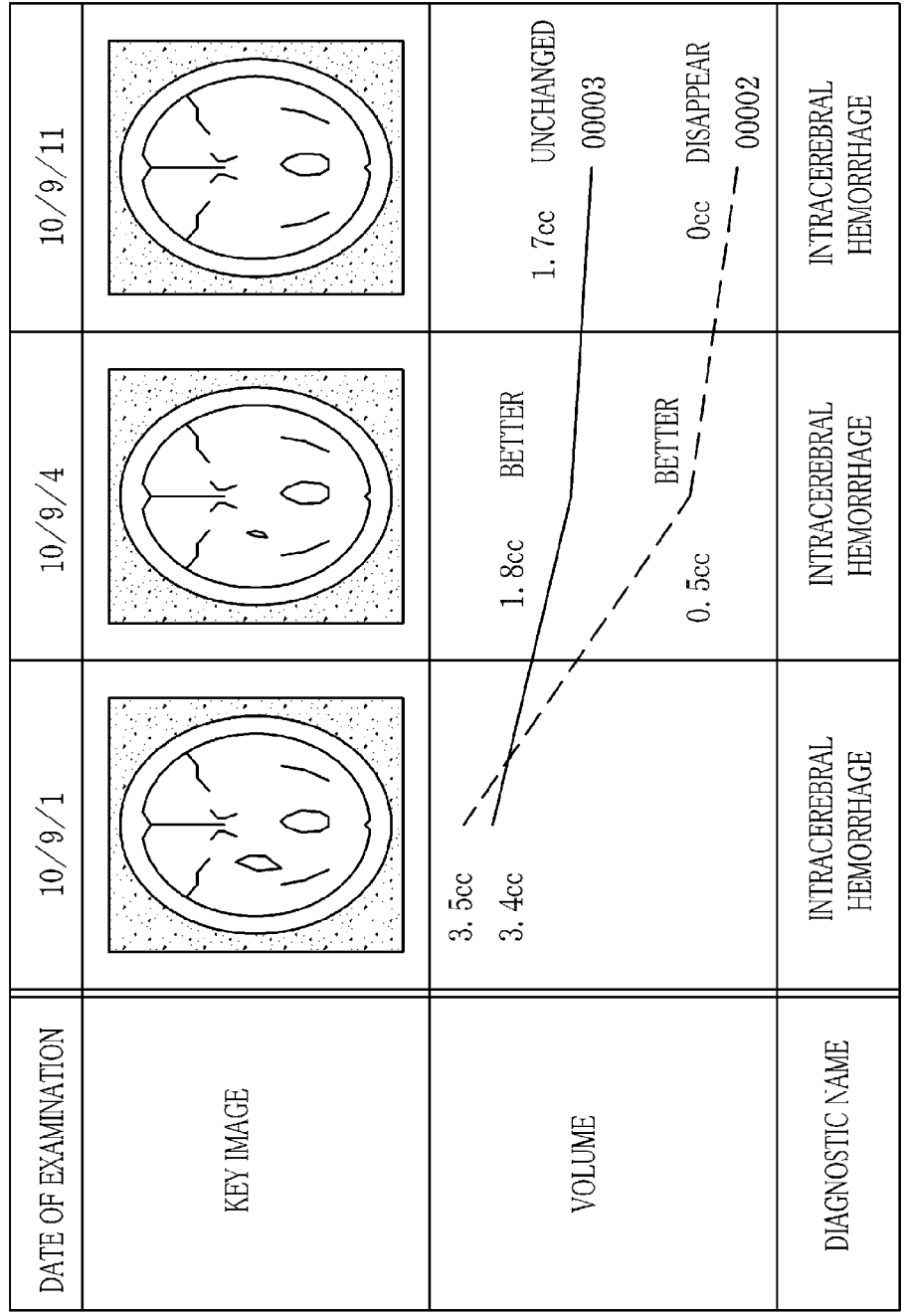

| CONDITION OF SELECTIVE INPUT | CERTAINTY | DIAGNOSTIC NAME | NUMBER OF INPUTS | PERCENTAGE (%) | ... |
|---|---|---|---|---|---|
| ... | | | | | |
| NUMBER:SINGLE BORDER:UNCLEAR MARGIN:IRREGULAR ABSORPTION:HYPODENSE | DEFINITE | HEPATOCARCINOMA | 20 | 40 | |
| | | HEPATIC ANGIOMYOLIPOMA | 10 | 20 | |
| | | ... | | | |
| SIZE: MAXIMUM LENGTH IS 30 MM OR MORE MINIMUM LENGTH IS 20 MM OR MORE | SUSPECTED | HEPATOCARCINOMA | 14 | 25 | |
| | | HEPATIC ANGIOMYOLIPOMA | 12 | 21 | |
| | | ... | | | |
| | EXCEPTION | HEPATOCARCINOMA | 7 | 10 | |
| | | HEPATIC HEMANGIOMA | 16 | 23 | |
| | | ... | | | |
| ... | | | | | |
| MARGIN:POORLY-DEMARCATED SURFACE:ROUGH DEGREE OF SWELLING:MODERATE SITE OF SWELLING:ENTIRE LIVER CONTRACTION:NO PARENCHYMA HOMOGENEITY:HETEROGENEOUS PARENCHYMA DENSITY:HIGH | DEFINITE | CIRRHOSIS | 50 | 85 | |
| | SUSPECTED | ... | ... | | |
| | EXCEPTION | ... | | | |
| ... | | | | | |

FIG.32 ~106

| DIAGNOSIS | CONDITION OF SELECTIVE INPUT | | LIKELIHOOD |
|---|---|---|---|
| HEPATOCARCINOMA | NUMBER:SINGLE BORDER:UNCLEAR MARGIN:IRREGULAR ABSORPTION:HYPODENSE | SIZE:MAXIMUM LENGTH IS 30 MM OR MORE MINIMUM LENGTH IS 20 MM OR MORE | 0.2 |
| | NUMBER:SINGLE BORDER:UNCLEAR MARGIN:IRREGULAR ABSORPTION:HYPODENSE | SIZE:MAXIMUM LENGTH IS LESS THAN 30 MM MINIMUM LENGTH IS LESS THAN 20 MM | 0.15 |
| | NUMBER:SINGLE BORDER:UNCLEAR MARGIN:IRREGULAR ABSORPTION:ISODENSE | SIZE:MAXIMUM LENGTH IS 30 MM OR MORE MINIMUM LENGTH IS 20 MM OR MORE | 0.1 |
| | ... | ... | |
| HEPATOBLASTOMA | NUMBER:SINGLE BORDER:UNCLEAR MARGIN:IRREGULAR ABSORPTION:HYPODENSE | SIZE:MAXIMUM LENGTH IS 30 MM OR MORE MINIMUM LENGTH IS 20 MM OR MORE | 0 |
| | NUMBER:SINGLE BORDER:UNCLEAR MARGIN:IRREGULAR ABSORPTION:HYPODENSE | SIZE:MAXIMUM LENGTH IS LESS THAN 30 MM MINIMUM LENGTH IS LESS THAN 20 MM | 0 |
| | NUMBER:SINGLE BORDER:UNCLEAR MARGIN:IRREGULAR ABSORPTION:ISODENSE | SIZE:MAXIMUM LENGTH IS 30 MM OR MORE MINIMUM LENGTH IS 20 MM OR MORE | 0.4 |
| | ... | ... | |

FIG.33

DIAGNOSTIC CANDIDATES

- SELECT DIAGNOSTIC NAME

| CERTAINTY | DIAGNOSTIC CANDIDATES | NUMBER OF INPUTS | LIKELIHOOD | |
|---|---|---|---|---|
| DEFINITE | HEPATIC ANGIOMYOLIPOMA | 20 | 0.2 | ☐ |
| | HEPATOCARCINOMA | 20 | 0.1 | ☐ |
| | HEPATOBLASTOMA | 2 | 0.4 | ☐ |
| SUSPECTED | HEPATIC ANGIOMYOLIPOMA | 42 | 0.2 | ☐ |
| | HEPATOCARCINOMA | 40 | 0.1 | ☐ |
| | HEPATIC HEMANGIOMA | 12 | 0.2 | ☐ |
| EXCEPTION | HEPATOCARCINOMA | 35 | 0.1 | ☐ |
| | HEPATIC HEMANGIOMA | 30 | 0.2 | ☐ |
| | HEPATIC ANGIOMYOLIPOMA | 5 | 0.2 | ☐ |

OK — 102
CANCEL — 104

APPARATUS, METHOD AND PROGRAM FOR ASSISTING MEDICAL REPORT CREATION AND PROVIDING MEDICAL INFORMATION

BACKGROUND OF THE INVENTION

1. Field of the Invention

The present invention relates to an apparatus, a method and a program for assisting medical report creation, wherein a sentence may be created on the basis of those words and clauses which are selectable from multiple options. The present invention also relates to an apparatus, a method and a program for providing doctors with medical information, including information on the course of a selected pathological lesion or diagnostic names of diseases inferred as candidates.

2. Description of the Related Art

Many kinds of computer systems are being introduced into medical fields in order to handle medical documents such as charts and reports in the form of electronic data. These computer systems are intended to facilitate creation and management of the medical documents and thus ease the labor of doctors who are in charge of making medical reports.

JPA 2009-271620 suggests creating a medical report using an electronic dictionary and a template. The dictionary registers those terms expected to be used in medical reports. The doctor who reads radiographic images can write a sentence to report findings just by mechanically operating selection buttons to fill appropriate terms in the template.

JPA 2008-176596 discloses simplifying fill-in operation in electronic medical charts by setting several tabs for each sheet file that formats entry of contents into the charts, and adding a new tab or making a copy of a tab.

JPA 2002-203045 suggests providing a button for adding items about medical history and drug allergies of a patient to an electronic medical chart of the patient. Upon clicking on this button, selectable items pop up on a screen.

JPA 2009-080731 provides a text box for writing findings to each affected part or lesion found in a radiogram, each text box being given an ID. After an examination for follow-up observation, a copy of the previous medical report of the same patient is utilized for reporting findings on the same affected part identified by the same text box ID. Thus the findings on the same affected part of the same patient are associated with each other at different times. Making use of this association, numerical information or the like can be extracted from the reports made at different times, to detect chronological changes in symptoms of each individual affected part from the extracted information and to display them in a table.

JPA 2005-510326 discloses a method of creating a medical report based on a structured report creation paradigm. Upon clicking on an external feature such as a lesion in an image, coordinate values of the clicked point and the number of the clicked image will be stored in a database. Findings in a series of follow-up observations may be horizontally liked or associated with each other by drag-and-drop or copy-and-paste. With respect to the associated findings, disease course information acquired from the follow-up observations, such as change in size of the lesion, can be displayed as images and numerical data.

JPA 2009-082442 discloses a diagnostic assisting apparatus which is provided with a data base containing case data including fixed results of diagnoses, and a medical knowledge database for managing data for each type of disease, including the size of lesion, the stage of disease, the severity of illness etc. According to input search criteria including data acquired from medical examinations, data relating to inferred diseases or disease course information may be retrieved from these data bases and displayed on a monitor. In this prior art, a text entered as findings through a designated format or template for a medical report is analyzed using a thesaurus and the like to produce finding data. According to differences between the produced finding data and the retrieved data relating to inferred diseases, the retrieved data is narrowed down to choose data of a disease to be displayed as most relevant. In an example of search results, the size, location and shape of a lesion are displayed as data relating to an inferred disease.

JPA 2007-018460 discloses a diagnoses assisting system that extracts keywords from sentences written as findings in a medical report and memorizes the keywords in association with the diagnostic name of disease and the degree of conviction on the diagnosis. Thereby, the system can infer some diseases as candidates according to newly-input findings. In this prior art, phrases or terms are clipped out of hand-written findings through character recognition, and synonyms are converted into a unique phrase. Then, the converted phrases are compared with keywords which are each associated with a disease, thereby to name one or more diseases as candidates inferred from the written findings.

JPA 2008-027099 discloses a diagnostic assisting system that memorizes a main complaint or symptoms in combination with the name of disease diagnosed for these symptoms each time a doctor writes the symptoms in a medical chart, and registers diagnostic frequency indicating how many times the doctor has provided the same diagnosis on these symptoms in the past. Based on the memorized data, some diseases may be extracted and suggested as candidates according to symptoms written in a medical chart. The diagnostic frequency data will be updated for each particular disease, and the candidates are chosen depending on the diagnostic frequencies. The symptoms may for example be entered through hand-writing or template-input. As for the hand-written entries, sentences reporting the symptoms are subdivided into individual words, and the words are evaluated.

One of the most labor-consuming works for the doctors who read radiographic images and create a medical report on findings is to write about multiple lesions. Multiple lesions can include ones having totally different features or partly different features, or ones approximately equal in feature but different in size or in site where the lesions are found. In that case, the doctors are required to write about findings on each of the multiple lesions. Writing or inputting the findings on each individual lesion from scratch will take a lot of work and time.

Although the above mentioned JPA 2009-271620 suggests using template operation tools for reducing load on the doctors in creating medical reports, this prior art mentions nothing about entry of findings on multiple lesions. Likewise, neither JPA 2008-176596 nor JPA 2002-203045 discloses anything about entry of findings on multiple lesions, although they suggest adding or copying the tabs or providing the addition button in order to improve the operability. Moreover, the latter two prior arts relate to an electronic chart not to an invention for assisting creation of medical reports.

In a follow-up observation, which may be executed for example for the purpose of judging therapeutic efficacy, a doctor generally checks changes over time in symptomatic state of a lesion when creating an examination report on this lesion. Therefore, providing time course of past examinations and illness trajectories as disclosed in the above mentioned JPA 2009-080731, JPA 2005-510326 and JPA 2009-082442 is useful for the doctor to create a medical report efficiently. In addition, it is possible to conduct a medical session with a patient while showing trajectories of a disease or lesion of the patient and other course information on other patients of the same or similar disease, in order to facilitate obtaining informed consent from the patient.

However, if the provided information on the course of the disease is not adequate or reliable, the doctor may not be able to diagnose the disease correctly. Also the informed consent cannot be appropriate if it is based on inadequate information.

According to the invention disclosed in JPA 2009-080731, the adequacy and reliability of illness course information depend on accuracy of extraction of numerical information from the observation report input in the text box. Also the invention disclosed in JPA 2009-082442 cannot secure the authenticity of data retrieved as relating to inferred diseases if any of various analyses of medical examination data, such as CAD or morphological analysis, is insufficient in performance, and hence search keys obtained from these analyses are inaccurate. Therefore, high-performance analyses are essential for this prior art.

Although JPA 2005-510326 recites displaying illness course information, it does not particularly describe how and where such information can be retrieved from.

Accordingly, any of the above mentioned prior arts cannot sufficiently satisfy the need for boosting authenticity of illness course information so as to lower incidence of medical malpractice such as misdiagnosis.

In the invention disclosed in JPA 2007-018460, phrases or terms are clipped out of sentences written as findings in a report, and synonyms of the clipped phrases or terms are converted into a unique phrase, to compare the clipped and converted phrases with keywords that are each associated with a disease, in order to infer one or more disease candidates. Since the phrases or terms are clipped out through character recognition, the adequacy and reliability of the diagnostic candidates depend on the accuracy of character recognition, which tends to be insecure.

The system disclosed in JPA 2008-027099 is not for assisting medical report creation, but it is intended to assist a doctor with diagnosis based on main complaint written in a medical chart. Although this system infers a disease from written symptomatic state and names it as a candidate, the symptomatic state can only be input by selecting from among prepared sentences expressing symptoms on a simple template. Because more than one sentence having a relatively complicated structure, including many modifying words expressing sizes or body parts, is needed to report the findings on medical reports, the simple template used in this prior art is inapplicable to medical reports.

Accordingly, any of the above mentioned prior arts, even in combination, cannot sufficiently satisfy the need for boosting authenticity of data of inferred disease candidates on making medical reports, and thus lowering probability of improper diagnoses.

SUMMARY OF THE INVENTION

In view of the foregoing, an object of the present invention is to provide an apparatus, a method and a program for assisting medical report creation, which allow doctors to create medical report more easily and efficiently.

Another object of the present invention is to make more adequate and more reliable medical information available to doctors for more accurate diagnoses.

To achieve the above and other objects, in one aspect of the present invention, an apparatus for assisting creation of a medical report containing a comment on a lesion comprises a display control device and a first storage device. The display control device is for displaying a template and an operational command input device as graphical user interfaces on a screen, the template being used for selectively inputting at least some of those words and phrases which constitute the comment. The first storage device stores rendering data of the template. The display control device displays an additional template on the screen on the basis of the rendering data in response to an addition command input through the operational command input device.

The addition commands may include a command to add a new template where no selection or input has been made, a command to make a copy of the presently displayed template.

Preferably, the display control device displays the additional template as an additional tab panel.

Preferably, the template is subdivided into multiple description areas for describing various items, and wherein addition commands from the operational command input device includes a command to add a new description area in the presently displayed template, and the display control device responsively provides the new description area in the presently displayed template.

In another aspect of the present invention, a medical information providing apparatus comprises a storage device for storing selective input data on a lesion in a database in association with a lesion ID given to each individual lesion, the selective input data being entered through a template for selectively inputting at least some of those words and phrases which constitute a comment on the lesion; a search device for searching the database for data of past medical reports relating to a desired lesion in response to a search request, and extracting course information presenting a change over time of the desired lesion from the data of the past medical reports; and a display control device for displaying the course information on the desired lesion.

Preferably, the search device can retrieve selective input data of a past medical report relating to a lesion to be described in a present medical report. In that case, the display control device can display, on the basis of the retrieved selective input data, a copied template that reproduces the same condition of selective input on a template used on creating the past medical report. Thus a new set of selective input data on the same lesion may be input through the copied template in the present medical report, and the storage device stores the new set of selective input data entered through the copied template in association with the same lesion ID as associated with the selective input data of the past medical report. If the database does not contain any selective input data that relate to the same lesion as described in the present medical report, the storage device issues a new lesion ID to store the selective input data of the present medical report in association with the new lesion ID.

Preferably, the display control device can list the course information to display. If the search device extracts the course information on a plurality of cases, the display control device preferably displays the course information of these cases in a comparable manner. If the extracted course information includes numerical values, the display control device preferably displays the course information in a graph plotting the numerical values along a time axis.

According to still another aspect of the present invention, a medical information providing apparatus comprises a first display control device for displaying a medical report editing screen having a selective data input area for selectively inputting at least some of those words and phrases which constitute a comment on findings and a diagnosis input area; a storage device for storing selective input data entered through the selective data input area in a first database in association with a diagnostic name entered through the diagnosis input area; a search device for searching the first database in response to a search request that provides the entered selective input data as a search key, to extract those diagnostic names which are association with identical or similar selective input data to the search key; and a second display control device for displaying the extracted diagnostic names.

Preferably, the diagnosis input area may be provided with a graphical user interface for selectively inputting the degree of certainty on the diagnostic name. In that case, the storage device may sort the diagnostic names by the selected degrees of certainty in the first database, and the second display control device may display the diagnostic names in order of certainty.

Alternatively, the storage device may register the number of times each individual diagnostic name has been input in the first database. If a diagnostic name to be stored in association with a set of selective input data has already been stored in association with an identical or similar set of selective input data, the storage device increments the number of times this diagnostic name has been input, and if not, the storage device creates a new area in the first database for registering the diagnostic name and the number of times the diagnostic name has been input. When a diagnostic name is extracted, the number of times the diagnostic name has been input or the percentage of the number of input times of the diagnostic name to the total number of input times may also be retrieved and displayed along with the extracted diagnostic name.

It is also preferable to store diagnostic names, each in association with at least a set of selective input data and likelihood of inferring the diagnostic name from the associated set of selective input data. When the search device extracts at least a diagnostic name based on the search key, the search device may also extract the likelihood of inferring the extracted diagnostic name from the selective input data that are identical or similar to the search key. Then the display control device may display the extracted diagnostic name along with the likelihood.

A method of assisting medical report creation of the present invention, which allows doctors to create medical report more easily and efficiently, will be specifically disclosed in the following detailed description of the preferred embodiments.

Also methods of providing medical information of the present invention, which provide more adequate and more reliable medical information for more accurate diagnoses, will be specifically disclosed in the following detailed description of the preferred embodiments.

BRIEF DESCRIPTION OF THE DRAWINGS

The above and other objects and advantageous features of the present invention will be more apparent from the following detailed description of preferred embodiments when read in connection with the accompanied drawings, wherein like reference numerals designate like or corresponding parts throughout the several views, and wherein:

FIG. 4 is an explanatory diagram illustrating an example of lesion describing template;

FIG. 5 is an explanatory diagram illustrating the operation for adding a plain lesion describing template or copying an edited page of lesion describing template;

FIG. 6 is an explanatory diagram illustrating an added plain lesion describing template;

FIG. 7 is an explanatory diagram illustrating a copied lesion describing template;

FIG. 12 is an explanatory diagram illustrating an example of lesion describing template;

FIG. 13 is an explanatory diagram illustrating an added plain lesion describing template;

FIG. 14 is an explanatory diagram illustrating a copied lesion describing template;

FIG. 15 is an explanatory diagram illustrating an example where a new description area is added to the lesion describing template;

FIG. 18 is an explanatory diagram illustrating an example of the lesion data table;

FIG. 19 is an explanatory diagram illustrating an example of a course information list;

FIG. 20 is a diagram illustrating a display style of course information;

FIG. 28 is an explanatory diagram illustrating an example of the diagnostic data table;

FIG. 32 is an explanatory diagram illustrating an example of a likelihood data table; and FIG. 33 is an explanatory diagram illustrating an example of another diagnostic candidate display window showing the likelihood of each diagnostic candidate.

DETAILED DESCRIPTION OF THE PREFERRED EMBODIMENTS

Figure 1:
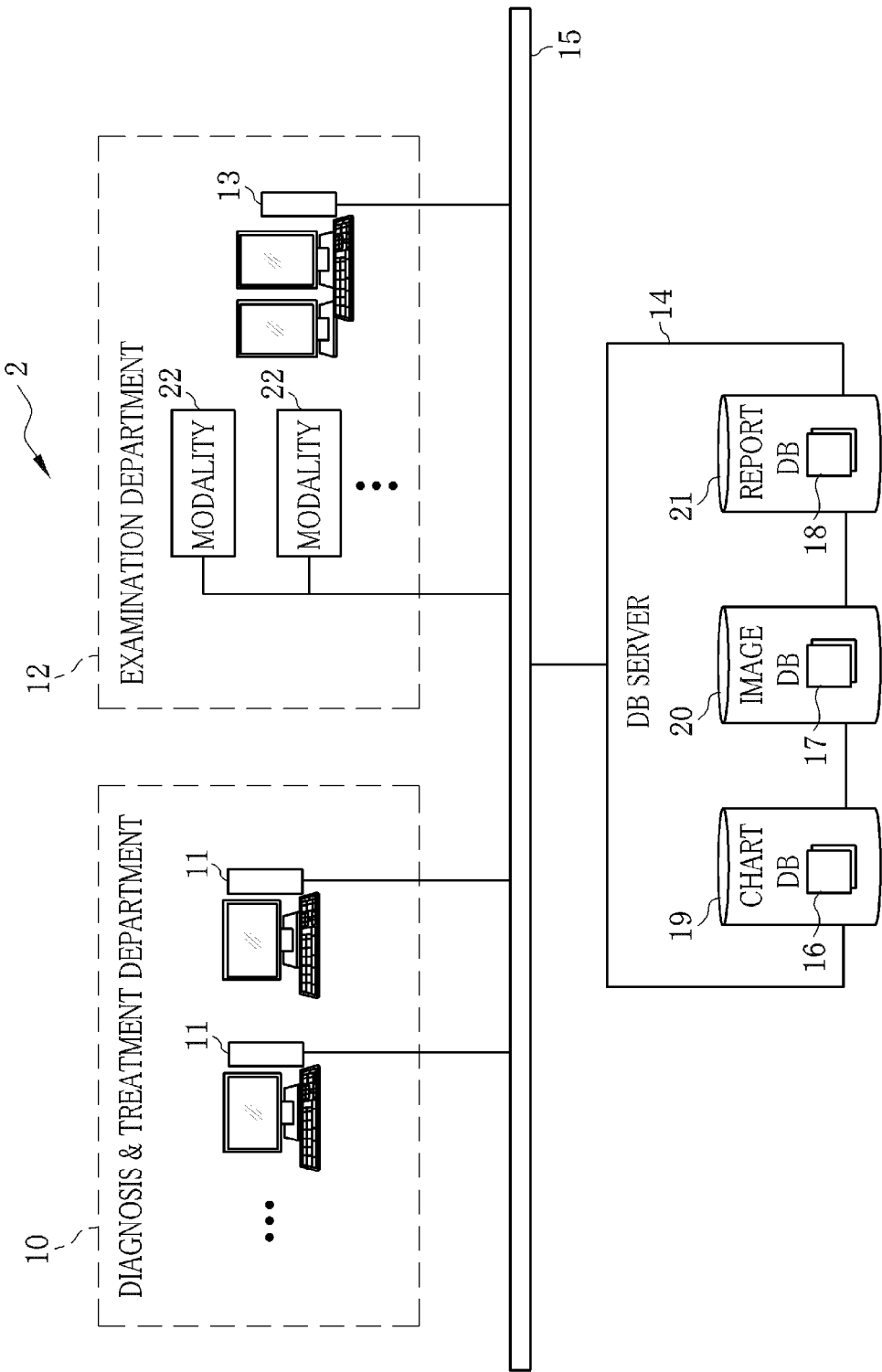
FIG. 1 is a diagram illustrating a structure of a medical information system.

In FIG. 1, a medical information system 2 is developed in a medical facility like a hospital, and consists of clinical terminals 11 installed in each diagnosis and treatment department 10, at least a report creation terminal 13 installed in a radiological examination department 12, and a database server 14, which are communicably connected to each other via a network 15. The network 15 may for example be a LAN (local area network) developed in the hospital.

The terminal 11 is operated by a doctor of the diagnosis and treatment department 10 to request a medical examination or a radiological interpretation. The terminal 11 is available for browsing or inputting medical charts 16, as well as for issuing a request for an examination to the examination department 12. The terminal 11 may display images 17 obtained through examinations or medical reports 18, which are provided from the examination department 12, so that doctors may refer to them in the diagnosis and treatment department 10.

The report creation terminal 13 is operated by a doctor of the examination department 12 who is in charge of reading radiographic images. The doctor of the examination department 12 may use the report creation terminal 13 for checking requests for examinations, and making medical reports 18 on the examinations. The report creation terminal 13 may display images obtained through examinations or a report edit screen 44 (see FIG. 3) for assisting the doctors with the medical reports 18.

The database server 14 has multiple databases including a chart database 19, an image database 20, a report database 21, etc. The chart database 19 contains data of medical charts 16 on individual patients. The image database 20 contains data of examination images 17 captured by modalities 22 in the examination department 12, such as CR, CT, MRI etc. The report database 21 contains data of medical reports 18 that have been created on the report creation terminal 13.

The database server 14 receives data of examination images 17 from the modalities 22 through the data bus 15, and stores the received data in the image database 20. The database server 14, therefore, functions as a server of so-called PACS (picture archiving and communication systems), and constitutes the PACS in combination with the modalities 22.

The data of examination images 17 have an image ID for identifying each individual examination image 17. For example, the data of each examination image 17 is stored as a file in the image database 20 in a file format conformable to DICOM (digital imaging and communication in medicine). Each file of the examination image 17 is accompanied with a DICOM tag that records accessory information including a patient ID, an examination ID, the date of examination, and the kind of examination. The data of examination images 17 is retrievable from the image database 20 using any of the various items in the DICOM tag as search keys.

The database server 14 constitutes a chart system in corporation with the terminal 11 and the chart database 19. The database server 14 also constitutes a report creation assisting system in corporation with the report creation terminal 13, the image database 20 and the report database 21. Like the data of examination images 17, data of each report 18 is retrievable using search keys including an examination ID, a patient ID, a patient name, etc. Although the respective databases are incorporated into the single server 14 in the illustrated embodiment, the databases may be installed separately in different database servers.

Each request from the terminals 11 contains various items recording patient ID, patient name, issue date of request, requester, requested type of examination (CT, MRI, etc.), and objects of the examination, as well as whether the requester requires the examination department 12 to conduct radiographic interpretations. The items recording the requester include the department the requesting doctor belongs to, the name of requesting doctor, and an ID of the requesting doctor. As the objects of the examination, judgment on therapeutic efficacy to a focus under treatment, or metastasis survey may for example be recorded.

The order from the terminal 11 is transmitted to an order reception terminal (not shown) in the examination department 12. The order reception terminal gives an examination ID to each received request for examination and manages data of these requests. The given examination ID is sent back to the terminal 11 along with an acknowledgement. Then, according to the requested order, a radiologist conducts imaging of a patient by a designated one of the modalities 22 in the examination department 12.

If the order contains a request for a radiographic interpretation on images obtained through an examination, the order is transmitted with its examination ID from the order reception terminal to the report creation terminal 13. Then a doctor in charge of radiographic interpretation checks the received order through the report creation terminal 13, and reads out data of related examination images 17 from the image database 20. The results of interpretation on these examination images 17 are concluded into a report 18.

At the completion of the report 18, the reading doctor sends a notice of completion of the report from the report creation terminal 13 to the terminal 11 of the requester. The notice of completion may include respective addresses of the examination images 17 and the report 18 in the databases 20 and 21. Thus, the requesting doctor may access from the terminal 11 to the addresses indicated in the notice of completion, to watch the examination images 17 and read the report 18.

These terminals 11 and 13 and the database server 14 are each embodied by installing control programs, such as operating systems, and applications, such as client programs or server programs, in a basic computing device like a personal computer, a server computer or a work station.

Figure 2:
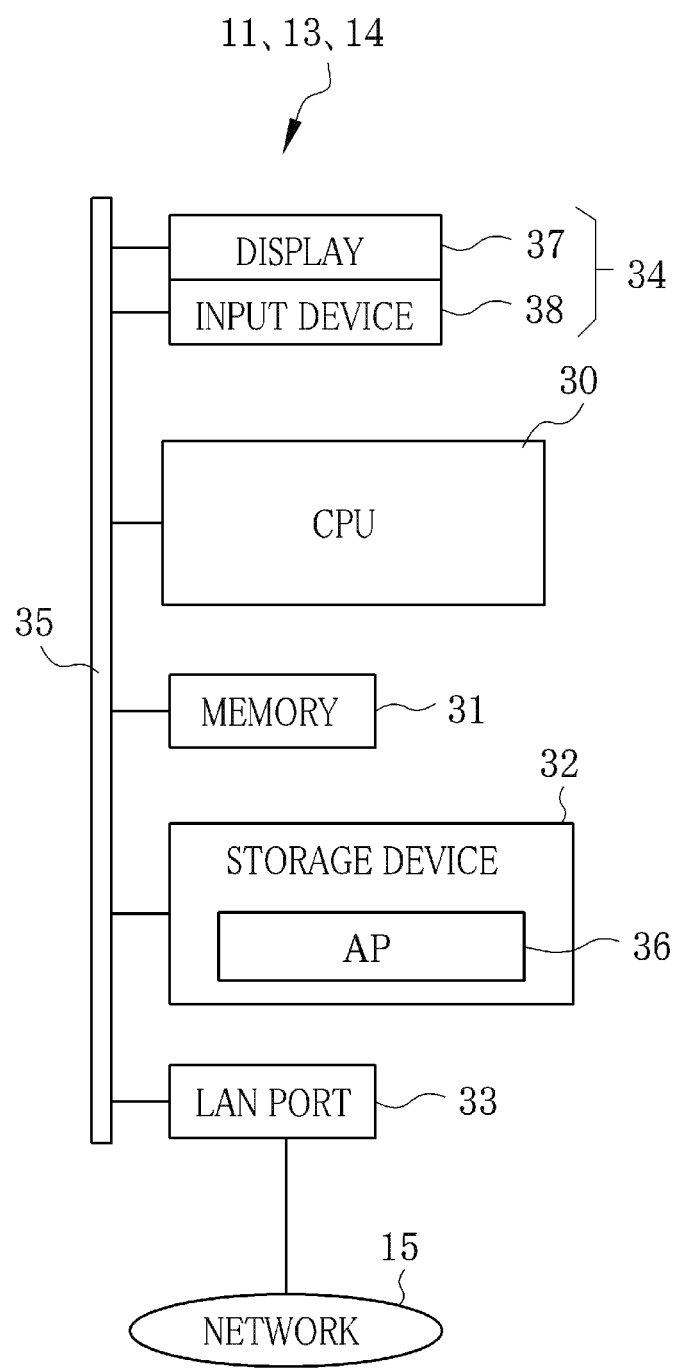
FIG. 2 is a block diagram illustrating a schematic structure of a computer applied to each of terminals and servers constituting the medical information system.

As shown in FIG. 2, the computing devices that constitute the terminals 11 and 13 and the database server 14 may have the same basic structure consisting of a CPU 30, a memory 31, a storage device 32, a LAN port 33, and a console 34, which are connected to each other through a data bus 35.

The storage device 32 may for example be a HDD (hard disc drive). The storage device 32 contains control programs, applications 36 and rendering data 65 (see FIG. 5). The rendering data 65 defines the type, layout, size, color and other factors of GUI (graphical user interface) for each of a variety of operational screens to be displayed on a monitor 37. In addition, the storage device 32 of the report creation terminal 13 contains definitions (not-shown) for creating a sentence as a comment on findings according to data input through the GUI, as set forth in detail later. The storage device 32 corresponds to a first storage device of the present invention.

Moreover, the database server 14 is provided with another storage device 32 as the databases separately from the HDD for storing programs. For example, the storage device 32 may be a disc array having multiple HDD connected in an array. The disc array may be incorporated into a main body of the database server 14 or may also be provided as a separate part connectable through a cable or a network to the main body.

The memory 31 is a work memory for the CPU 30 to execute work processing. The CPU 30 loads an appropriate control program from the storage device 32 to the memory 31, to execute processing according to the loaded program. Thus the CPU 30 comprehensively controls the respective components of the computer. The memory 31 stores temporary data 66 (see FIG. 5) that represent the state of selection on the term selection buttons 51 (see FIG. 3). The memory 31 corresponds to a second storage device of the present invention.

The LAN port 33 is a network interface controlling transmission through the data bus 15. The console 34 consists of the monitor 37 and input devices 38 including a keyboard and a mouse.

Applications 36 installed in the terminal 11 include client programs such as software for browsing and editing medical charts 16 and viewer software for browsing examination images 17 and medical reports 18. When one client program is activated, the monitor 37 of the terminal 11 displays a GUI operation screen. The operation screens include display screens for displaying a medical chart 16, examination images 17 and a medical report 18, which are respectively read out from the chart database 19, the image database 20 and the report database 21.

Through the input devices 38, the terminal 11 is fed with commands for inputting or editing data of medical charts 16 or commands for inputting or issuing an order or request to the examination department 12. The input data of medical charts 16 or the order are stored in the chart database 19.

Applications 36 installed in the report creation terminal 13 include a report editing client program for creating and editing a medical report 18. According to this report editing client program, the report creation terminal 13 executes processing for displaying examination images 17 and editing a medical report 18. Applications 36 installed in the database server 14 include a server program for executing processing in response to demands from the respective client terminals 11 and 13 and sending back the results of processing to these terminals.

Figure 3:
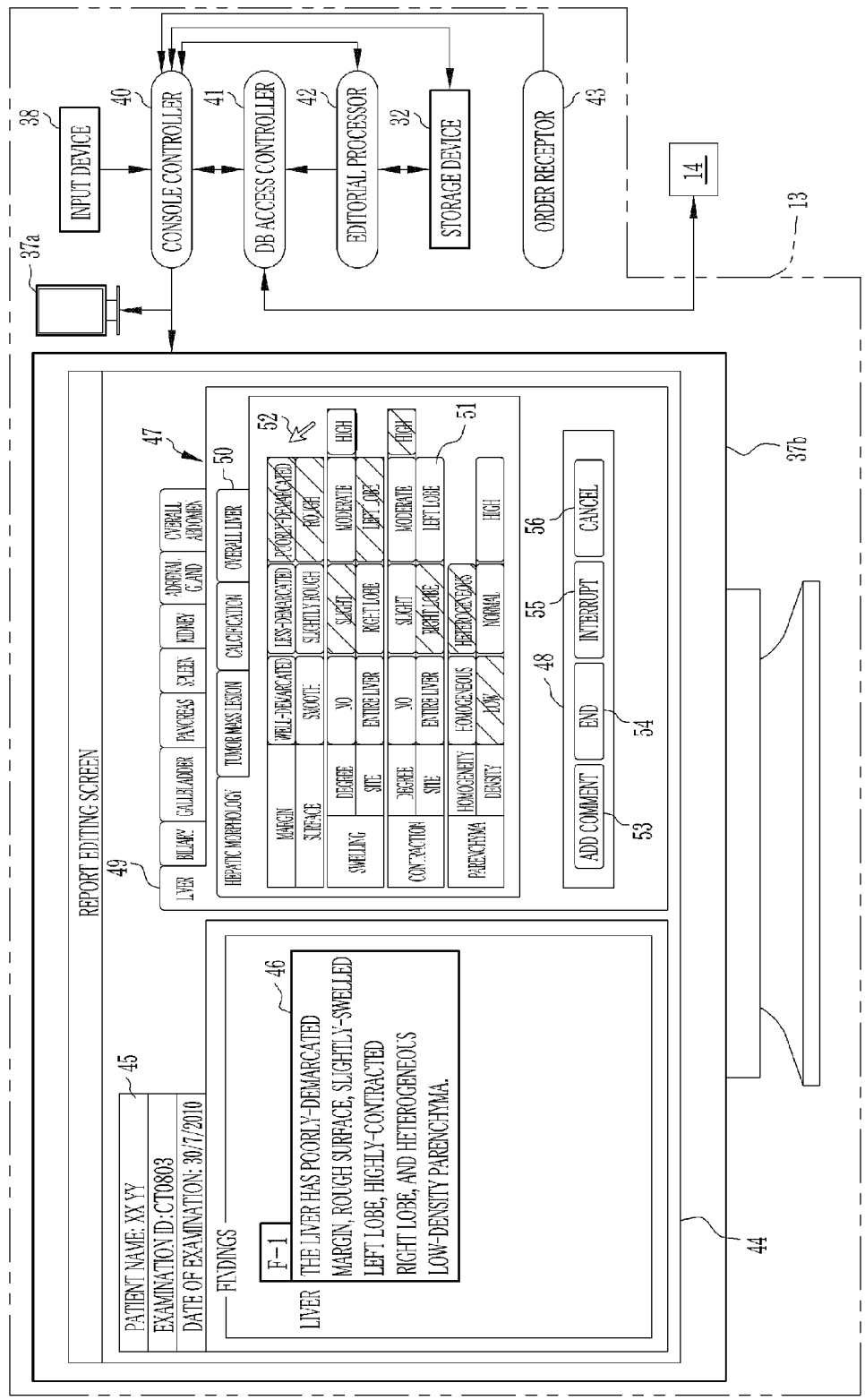
FIG. 3 is a diagram illustrating a schematic structure of a report creation terminal and an example of a report editing screen.

Referring to FIG. 3, the CPU 30 of the report creation terminal 13 functions as a console controller 40 (corresponding to a display controller), a database access controller 41, an editorial processor 42, and an order acceptor 43, when the report editing client program is activated. The order acceptor 43 accepts an order from the order reception terminal 11 through the data bus 15. The accepted order is registered in an order table that is not shown but may be provided for example in the storage device 32 of the report creation terminal 13.

The report creation terminal 13 is configured to have dual monitors 37a and 37b, which are connected to a terminal main body having the CPU 30. One monitor 37a outputs an image display screen for displaying examination images 17. The other monitor 37b outputs the report edit screen 44 for use in creating a report 18.

The image display screen and the report edit screen 44 individually constitute a GUI operation screen. The console controller 40 reads out rendering data 65 from the storage device 32, to output the operation screens to the respective monitors 37a and 37b on the basis of the read rendering data 65. The console controller 40 receives operation commands input from the input devices 38 through the operation screens.

The image display screen and the report edit screen 44 get active in cooperation with each other. When an examination ID is entered through the report edit screen 44 to designate examination images 17 to be interpreted, the console controller 40 retrieves data of the examination images 17 assigned by the entered examination ID from the image database 20. The console controller 40 activates the image display screen to output the retrieved examination images 17 on the monitor 37a.

On the image display screen, various kinds of examination images 17, such as ultrasonic images captured by an ultrasonograph, perspective radiographs captured by a CR (computed radiography system), tomographic images captured by a CT (computed tomography) system or a MRI (magnetic resonance imaging) system, or 3D (three-dimensional) images produced based on tomographic images, may be displayed. The image display screen is provided with a variety of operation tools, such as operation buttons, list boxes, and icons, which constitute a GUI. Through these operation tools, a variety of operation commands from the input devices 38 may be entered.

The report edit screen 44 includes a basic information display area 45, a comment input area 46, a selective term input area 47, and an operation button area 48. These areas constitute various operation tools of a GUI. Through these operation tools, a variety of operation commands from the input devices 38 may be entered. The operation commands entered on the report edit screen 44 include a command for reading data of a report 18 from the report database 21, a command for storing data of a report 18 in the report database 21, and a command for selectively activating the comment input area 46 to be ready for data entry.

The basic information display area 45 displays basic information items including a patient name, an examination ID (e.g. CT0803), the date of imaging the designated examination images 17 (e.g. Jul. 30, 2010). These basic information items are read out from an order for a medical report on the corresponding examination.

In the comment input area 46, a record of findings, such as state of a lesion, through observation of the examination images 17 by the radiological doctor is entered as text data or a written comment. Only one comment input area 46 is provided on the report editing screen 44 in the example of FIG. 3, but one or more comment input areas 46 may be added to it. For example, one comment input area 46 may be provided for one purpose of an examination, such as for judgment on therapeutic efficacy, and another comment input area 46 for another purpose of the same examination, such as for metastasis survey. It may also be possible to provide separate comment input areas 46 for different doctors who are in charge of radiological interpretation of the same examination images: a trainee doctor and a trainer doctor, or a doctor for a first opinion and a doctor for a second opinion.

The selective term input area 47 is an operation tool for inputting a comment in the comment input area 46 through mouse-clicking, and may also be called a template operation tool. The selective term input area 47 has large classification panels 49 classifying terms according organs such as "liver" and "bile duct", and small classification panels 50. The small classification panels 50 include those items typifying contents expected to be written as comments or findings for each organ, e.g. "hepatic morphology", "tumor mass lesion", etc. for "liver", as shown in FIG. 3. The name of the organ corresponding to the selected one of the large classification panels 49, i.e. "liver" in the illustrated example, is displayed beside the comment input area 46.

Each small classification panel 50 is provided with a plurality of term selection buttons 51. The term selection buttons 51 are arranged in rows, one row for one subdivided observation item such as "margin", "surface", "enlargement", "contraction", etc. For example, the row for the observation item "margin" includes terms "well-demarcated", "less-demarcated" and "poorly-demarcated", and the row for the observation item "surface" includes terms "smooth", "less smooth" and "rough". In addition, the observation items "swelling" and "contraction" include subsidiary items: "degree of swelling" and "swelled site", and "degree of contraction" and "contracted site". In the following description, the observation items and the subsidiary items will be commonly referred to as observation items inasmuch as discrimination between them is not necessary. The terms selectable by the term selection buttons 51 include those medical terms which are most frequently used in a comment with respect to the respective observation items. Moreover, all of the terms selectable by the term selection buttons 51 are modifiers that represent various degrees and geometries of each item to be observed and thus qualify the observation items.

A desired one of the term selection buttons 51 may be selected by clicking the mouse while putting a pointer 52 thereon. The term selection buttons 51 are selectable one for each observation item. For example, upon selecting the button "poorly-demarcated" while the button "well-demarcated" is selected in the observation item "margin", the selection of the button "well-demarcated" is automatically canceled.

On the basis of the terms selected through the term selection buttons 51, a comment is displayed in the comment input area 46 while the comment input area 46 is active. The operator may add some words and phrases to the displayed comment through the keyboard or the like.

The comment will be displayed in the comment input area 46 when at least one of the term selection buttons 51 is selected, and the comment will be revised upon each additional selection of the term selection buttons 51. Correspondingly, temporary data 66 representative of the selected state of the term selection buttons 51, which is stored in the memory 31, will be revised upon each additional selection of the term selection buttons 51. For example, the additional selection includes a case of selecting one term selection button 51 for a third observation item after selecting two term selection buttons 51 for first and second observation items respectively. The addition selection also includes a case of reselecting another button 51 after selecting one button 51 for the same observation item.

In FIG. 3, selected term selection buttons 51 are discriminated by hatching. Since the buttons 51 for "margin: well-demarcated", "surface: rough", "degree of swelling: slight", "swelled site: left lobe", "degree of contraction: high", "contracted site: right lobe", "parenchyma homogeneity: heterogeneous" and "parenchyma density: low" are selected in this instance, a comment "poorly-demarcated margin, rough surface, slightly-swelled left lobe, highly-contracted right lobe, heterogeneous low-density parenchyma" is displayed in the comment input area 46.

The operation button area 48 is provided with various types of operation buttons 53 to 56. Comment addition button 53 is for adding another comment input area 46. Upon clicking the mouse while putting the pointer 52 on the comment addition button 53, an additional comment input area 46 appears on the report edit screen 44.

Data of the comment input in one comment input area 46 is identified with a comment ID. The comment ID correlates the comment with the examination images 17 and the report 18. The comment ID includes a serial number assigned to each comment input area 46 in order of appearance. In this example, a comment input in the $N^{th}$ comment input area 46, N is a positive natural number above, will be given a comment ID "F-N". Therefore, a comment ID "F-1" is displayed on the upper side of the first comment input area 46 in FIG. 3.

Ending button 54 is for finishing editing the report 18. When the ending button 54 is selected, data of the report 18 is saved as final, being prohibited from further edition and thus protected from falsification. Interrupting button 55 is for interrupting creating the report 18 for a while. When the interrupting button 55 is selected, data of the report 18 is temporarily stored as unfinished. Cancel button 56 is selected to close the report edit screen 44.

The database access controller 41 sends requests for processing to the database server 14 according to a command from the console controller 40 or the editorial processor 42, and receives results of the processing from the database server 14. The requests include a search request for the image database 20, upon which the image database 20 is searched for an examination image using an examination ID or an image ID as a search key. The requests also include a saving request for saving data of the report 18 in the report database 21 and a search request for retrieving data of the report 18 from the report database 21.

The database access controller 41 receives data of the report 18 to be stored from the editorial processor 42, and sends the received data to the database server 14. The database access controller 41 also receives retrieved data from the database server 14 and transfers it to the console controller 40.

Upon executing a server program, the CPU 30 of the database server 14 functions as a data storage processor and a data retrieval processor for examination images 17 and reports 18. The data storage processor executes processing for data storage in the databases 20 and 21 according to the saving requests from the clients such as the report creation terminal 13 and the modalities 22. The data retrieval processor retrieves data from the databases 20 and 21 in response to requests from the terminals 11 and the report creation terminal 13, and sends back the requested retrieved data to the requesters.

The editorial processor 42 accepts text data of a comment written in the comment input area 46 of the report edit screen 44 as well as the selective input data, i.e. data on the selected states of the panels 49 and 50 and the term selection buttons 51 as well as data input in data entry boxes 61, via the console controller 40. The editorial processor 42 accepts these comment data as a block separated for each comment input area 46.

Then the editorial processor 42 gives a comment ID, e.g. "F-1", "F-2", etc., to each comment data block before registering it in the data of the report 18. Besides the comment data, the editorial processor 42 reads out information from the order, such as the examination ID, the patient ID and the patient name, and adds to the data of the report 18.

In addition to the comment ID, the editorial processor 42 gives a doctor ID to each comment data, which identifies the doctor who gave that comment. The doctor ID may be entered as an ID required for user authentication at the time of actuation of the report creation terminal 13. The comment data is thus retrievable using the comment ID or the doctor ID.

The editorial processor 42 produces a sentence as a comment corresponding to the selected state of the panels 49 and 50 and the selected state of the term selection buttons 51 according the definitions for comment description stored in the storage device 32. The definitions for comment description have data in a hierarchy consisting of items for organs, comments, observation and phrases for each observation item in this order from the top. The definitions for comment description define the position of clauses for respective observation items in a comment sentence, as well as the sequence of phrases within each clause of each observation item. For example, through the definitions for comment description, a comment sentence is divided into the subject and the predicate for each observation item, and the subject and the predicate are each divided into a main part and modifiers that modify the main part. Thus, all phrases constituting the comment sentence are sorted into the respective classes. The definitions for comment description further sort the main part of the predicate according to the position in the sentence and whether it is of an affirmative form or a negative form. In the example of FIG. 3, the predicate will take the negative form merely when "no" is selected in the term selection button 51 in the observation items "degree of swelling" and "degree of contraction". Other options are all affirmative.

Taking the observation item "swelling" for example, "entire liver", "right lobe" and "left lobe" are registered as input options for the subordinate item "site of swelling" as the modifier in the subject; "slight", "moderate" and "high" are registered as input options for the subordinate item "degree of swelling" as the modifier in the predicate; and ",", ".", "not," and "not." are registered as input options for the main part of the predicate. The option "," represents an intermediate position in the sentence and the affirmative form. The option "." represents the end of the sentence and the affirmative form. The option "not," represents an intermediate position in the sentence and the negative form. The option "not." represents the end of the sentence and the negative form.

When any of the term selection buttons 51 is selected, the editorial processor 42 looks up the definitions for comment description to read out those observation items corresponding to the selected state of the term selection buttons 51, which may be referred to as the active observation items, from the respective definition classes.

Thereafter, the editorial processor 42 decides a main part of the predicate of the active observation items. The editorial processor 42 confirms the position of each clause relating to the active observation item in the sentence and the form of the clause, i.e. affirmative or negative. Then the editorial processor 42 checks whether other observation items of the same hierarchical level as the active observation items are active or not in the order in which these items are registered in the definitions. If a first active observation item is followed by a second active observation item, the position of the first active observation item is determined to be "intermediate". Without any following active observation item, the position of an active observation item is determined to be "end".

If a phrase corresponding to a selected term selection button 51 is of negative form, that is, when "degree of swelling: no" or "degree of contraction: no" is selected, the editorial processor 42 judges that the item "swelling" or "contraction" should be used in the negative form. Otherwise, the editorial processor 42 judges the item to be used in the affirmative form. The editorial processor 42 thus reads out phrases from the respective classes of the definitions for comment description, and couples these phrases to each other in the order of registration in the definitions for comment description: modifiers of the subject, a main part of the subject, modifiers of the predicate, and a main part of the predicate.

The comment producing processes in the editorial processor 42 will be explained with respect to the example of FIG. 3. In this example, "liver" and "hepatic morphology" are selected among the panels 49 and 50, respectively, and the editorial processor 42 looks up the item "liver" and its subordinate item "hepatic morphology" in the definitions for comment description, to read out a main part of the subject, modifiers in the subject and the predicate, and other factors for each of the active observation items (throughput from "margin" to "parenchyma" in this case) from the definitions.

Since all the observation items are active in this case, the observation items from "margin" to "parenchyma homogeneity" are used in the intermediate positions of the sentence. Since neither "degree of swelling: no" nor "degree of contraction: no" is selected, these observation items are all used in the affirmative form. Accordingly, except the observation item "parenchyma density", the editorial processor 42 reads out the words to be used as main parts of the predicate in the intermediate position of the sentence in the affirmative form, selectively from the definitions for comment description. Coupling these words in the predetermined order produces the comment as shown in the comment input area 46 in FIG. 3.

In another example where only "margin: poorly-demarcated" is selected, a comment "The margin is poorly-demarcated." appears in the comment input area 46. When only "degree of swelling: no" is selected, a comment "No swelling is found." will be produced. When only "degree of contraction: moderate" and "site of contraction: entire liver" are selected, a comment "The entire liver is moderately contracted." will be produced. When only "parenchyma: heterogeneous" is selected, a comment "The parenchyma is heterogeneous." will be produced. If a single observation item is selected to be active, the subsequent comment will be a simple sentence. If a number of observation items are active, the subsequent comment will be a compound sentence consisting of clauses relating to the respective items.

Referring to FIG. 4, another example of the selective term input area 47 is illustrated which appears when the tab "liver" of the large classification panels 49 and a tab "tumor mass lesion" of the small classification panels 50 are selected. Hereinafter, the selective term input area 47 opened by selecting the tab "tumor mass lesion" of the small classification panels 50 will be called a lesion describing template 60.

In the lesion describing template 60, term selection buttons 51 for "irregular", "hypoechoic", etc. are arranged in rows according to observation items such as "shape", "internal echo", etc., like in the selective term input area 47 of FIG. 3. Regarding observation items "site", "size" and "infiltrated part", no term selection button 51 is provided, but instead, entry boxes 61 are provided for accepting keyboard-entry. An entry box 61 is also provided on the right side of an observation item "number". In these entry boxes 61, terms indicating the location of tumor mass lesion, such as "right lobe", "left robe", or "S1" to "S8", or numerical values indicating the size or the number of tumor mass lesion, such as "15", "10", or "3", may be entered by operating the keyboard. The entry box 61 on the right end of the observation item "number" will be used when multiple lesions are found in the examination image 17, and these lesions are in the same site, of the same size and aspects or features. According a definition for comment description on the lesion describing template 60, those parts of a sentence which are to be entered through the keyboard are registered as blanks.

In the example shown in FIG. 4, the term selection buttons 51 for "shape: irregular", "internal echo: hypoechoic", "echo pattern: mixed", "homogeneity: heterogeneous", "posterior echo: unchanged", and "bloodstream signal: few", "calcification: no" are selected, as implied by hatching. In addition, through the keyboard, a numeral or numerical values "S2" and "30 mm×20 mm" are entered in the entry boxes 61 for the observation items "site" and "size", respectively. The procedure of selecting the term selection buttons 51 and creating a comment sentence is equivalent to the procedure as described above with reference to FIG. 3.

On an upper area of the lesion describing template 60, a pull-down menu box 62 and a lesion addition button 63 are provided. The pull-down menu 62 is for adding a new page of lesion describing template 60 or copying an edited page of lesion describing template 60. When an inverted triangle beside the pull-down menu 62 is clicked on, options between "add-new" and "copy" are displayed in a pull-down menu. The lesion addition button 63 is operated to enter an instruction signal after either "add-new" or "copy" is selected from the pull-down menu 62.

When "add-new" is selected by the pull-down menu 62 and then the lesion addition button 63 is clicked on, an add-new signal is sent to the console controller 40, as shown in FIG. 5. Upon the add-new signal, the console controller 40 reads out rendering data of the lesion describing template 60 among the rendering data 65 stored in the storage device 32. This rendering data of the lesion describing template 60 represents a plain page of lesion describing template 60 that has no term selection button 51 selected and no data in the entry boxes 61.

On the basis of the read rendering data 65, the console controller 40 changes the display on the monitor 37b from the condition shown in FIG. 4 to the condition shown in FIG. 6. In FIG. 6, the console controller 40 displays an additional tab "#2" 68 of a new page of the lesion addition template 60 next to the tab "tumor mass lesion" in the small classification panels 50, the tab "tumor mass lesion" being of the default lesion describing template 60.

On the other hand, when "copy" is designated in the pull-down menu 62 and then the lesion addition button 63 is clicked on, a copy signal is sent to the console controller 40, as shown in FIG. 5. Then the console controller 40 reads out the rendering data 65 representative of the plain lesion describing template 60 from the storage device 32, like when it receives the add-new signal. In addition, the console controller 40 reads out temporary data 66 from the memory 31, the temporary data 66 indicate the latest state of the term selection buttons 51 which have been selected on the original page of lesion describing template 60.

Using the temporary data 66 and the rendering data 65, the console controller 40 reproduces the selected state of the term selection buttons 51 on a new page of lesion describing template 60. Thus the display on the monitor 37b changes from the condition shown in FIG. 4 to the condition shown in FIG. 7. An additional tab "#2" of a copied page of the lesion describing template 60 is designated by 69 in FIG. 7, because the copied page maintains the selected state of the term selection buttons 51 of the original as shown in FIG. 4, unlike the newly-added plain template page with the tab 68.

The mark "#2" on the tab 68 or 69 indicates that this panel is the second version of the default lesion describing template 60 that will initially be opened when the tab "tumor mass lesion" is clicked on. Accordingly, each time a page of lesion describing template 60 is newly-added or copied, the newly-added or copied page is sequentially tagged with a tab "#2", "#3", "#4" and so forth, and the tabs of the additional pages are added to one another following to the tab "tumor mass lesion" of the small classification panels 50. Note that it may also be possible to copy a newly-added page or recopy a copied page of the template after revising it by selecting or reselecting some term selection buttons 51 or inputting numerical values thereon.

Each of the newly-added or copied page of lesion describing template 60, which may also be referred to as the newly-added or copied panel tab 68 or 69, respectively, has a delete button 64 beside the lesion addition button 63. The delete button 64 is operated to delete the newly-added or copied panel tab 68 or 69.

Figure 8:
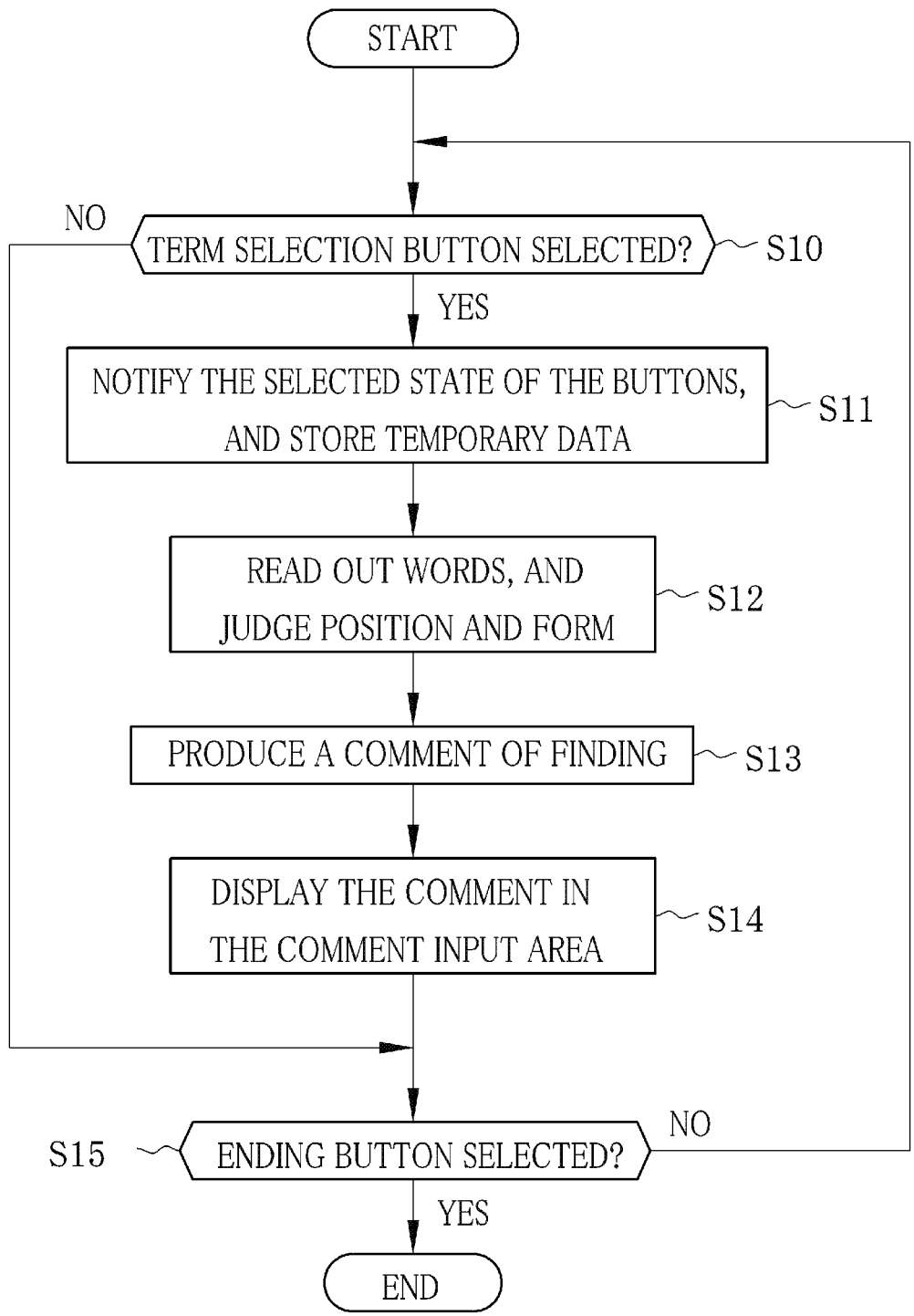
FIG. 8 is a flowchart illustrating a sequence of report creation processes.

Now the overall operation of the medical information system configured as above will be described with reference to the flowcharts of FIGS. 8 and 9.

Doctors may issue orders through the terminals 11 of the diagnosis and treatment department 10. The orders issued from the terminals 11 are received by the report creation terminal 13 via the order reception terminal in the examination department 12.

Doctors in the examination department 12 check the orders on the report creation terminal 13, to start creating medical reports 18. Synchronously with the report edit screen 44 being displayed on the monitor 37b, the image display screen is displayed on the monitor 37a. The doctor in charge of radiographic interpretation may input comments on a particular organ in the comment input area 46 on the report edit screen 44 while observing the particular organ in the examination images 17 on the image display screen.

The comment can be input by selecting appropriate ones of the term selection buttons 51 and inputting information in the entry boxes 61. When one of the term selection buttons 51 is selected, that is "yes" in the step S10 in FIG. 8, the console controller 40 notifies the editorial processor 42 of the state of data entry in the selective term input area 47, including the selected state of the panels 49 and 50 and the selected state of the term selection buttons 51. The state of data entry in the selective term input area 47 is also sent from the console controller 40 to the memory 31, to be stored as temporary data 66 therein (step S11).

Next the editorial processor 42 executes searching the definitions for comment description to read out phrases of the respective observation items from the definitions in accordance with the selected state of the term selection buttons 51 (step S12).

Thereafter the editorial processor 42 judges the position of each clause relating to the individual observation item and the form of the clause, i.e., affirmative form or negative form (step S12). Specifically, if a particular observation item is followed by an active observation item of the same hierarchal level, the position of the particular observation item is judged to be "intermediate". If not, the particular observation item is judged to be positioned in the end of a sentence. Moreover, if the form of an input phrase corresponding to a selected term selection button 51 is "negative", the phrase is judged to be used in the negative form. Otherwise, any input phrase is judged to be used in the affirmative form. According to the judgment on the position and the form of each clause, words and phrases are read out from the definitions for comment description, to constitute the main part of the predicate.

The read words and phrases are coupled to each other in the order predetermined by the definition for comment description, to produce a sentence (step S13). The produced sentence is transferred from the editorial processor 42 to the console controller 40, to be displayed in the comment input area 46 under the control of the console controller 40 (step S14). Thus the doctor can enter a comment sentence by selecting the term selection buttons 51. These processes are executed sequentially and repeatedly upon each selection of another one of the term selection buttons 51.

To complete entering the comments, the doctor selects the ending button 54 ("yes" in the step S15). When the ending button 54 is selected, the database access controller 41 sends the request for saving data of the report 18 to the database server 14. Upon the saving request from the report creation terminal 13, the database server 14 executes saving the data of the report 18 in the report database 21. Thus, one session of the report creating process is terminated.

When the report 18 is complete, the report creation terminal 13 sends a notice of completion to the terminal 11 of the doctor who requested the report 18. The requester makes an access to the report database 21 through the terminal 11, to read out the report 18 on the basis of the address of the report 18 that is indicated in the notice of completion. Then a report display screen displaying the report 18 and an image display screen displaying the related examination images 17 to the report 18 appear on the monitors 37 of the terminal 11, allowing the requester to read and check the contents of the report 18.

Figure 9:
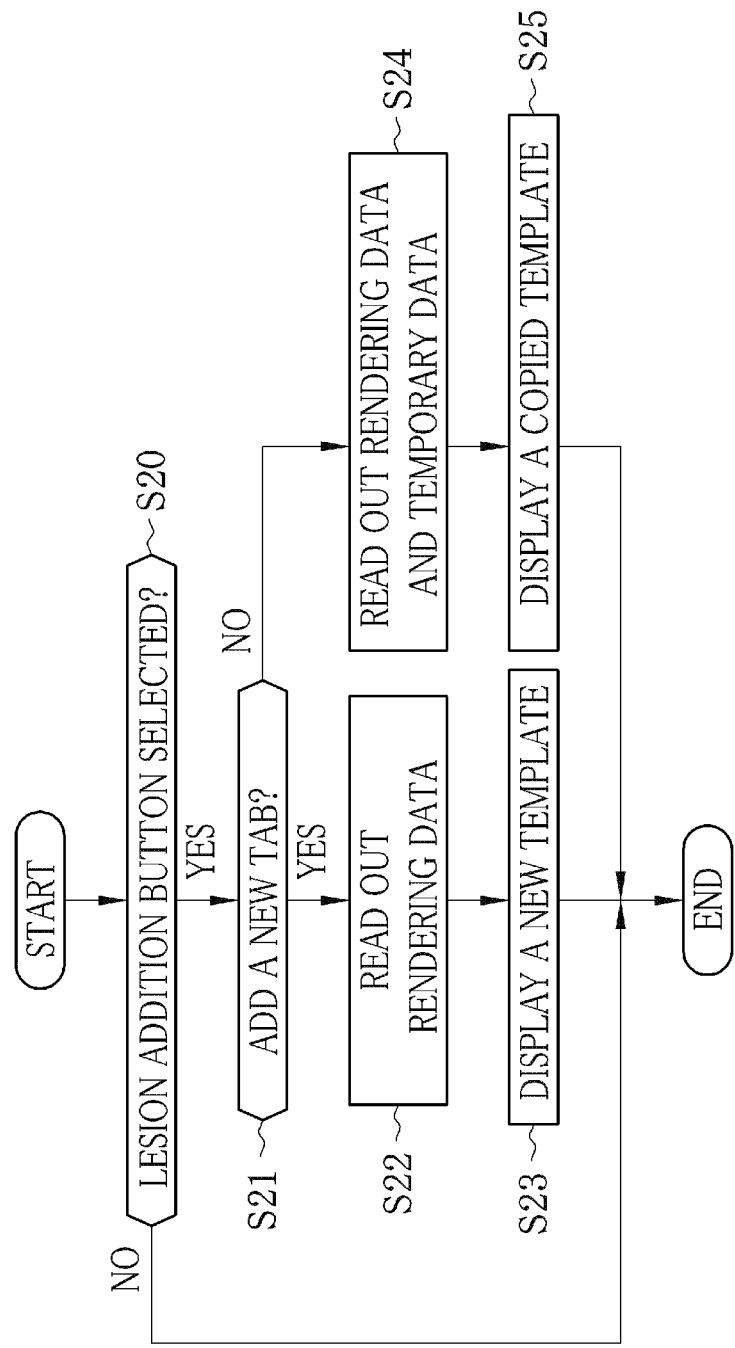
FIG. 9 is a flowchart illustrating a sequence of adding a new page of lesion describing template or a copied lesion describing template as an additional tab panel.

Referring to FIG. 9, when multiple lesions are found in a series of examination images 17 and these lesions have totally different features, e.g. some being solid tumor mass lesions whereas other being cystic tumor mass lesions, the radiographic interpreting doctor may select the option "add-new" in the pull-down menu 62 of the lesion describing template 60, and then click on the lesion addition button 63 ("yes" in the steps S20 and S21). Then the add-new signal is sent to the console controller 40, so the rendering data 65 of the plain lesion describing template 60 is read out from the storage device 32 (step S22). Based on the read rendering data, a newly-added plain page of lesion describing template 60 is displayed as a panel or tab 68 on the monitor 37b, as shown for example in FIG. 6 (step S23).

On the other hand, when multiple lesions found in a series of examination images 17 have partly different features from each other, the doctor may select the option "copy" in the pull-down menu 62 and then click on the lesion addition button 63 ("yes" in the step S20 and "no" in the step S21). Then the copy signal is sent to the console controller 40, and the rendering data 65 of the plain lesion describing template 60 and the temporary data 66 representative of the selected state of the term selection buttons 51 on the original edited template page are read out respectively from the storage device 32 and the memory 31 (step S24). Thus the console controller 40 displays a copied panel or tab 69 of the previously edited lesion describing template 60, where the same term selection buttons 51 as the original have been automatically selected on the basis of the temporary data 66, as shown for example in FIG. 7 (step S25).

As described so far, since the medical information system has the pull-down menu 62 and the lesion addition button 63, which allow designating adding another page of lesion describing template 60 or copying an already-edited page of lesion describing template 60 in the selective term input area 47 on the report edit screen 44, comments on the found lesions maybe entered more easily and efficiently through template operation tools.

Depending upon whether the found lesions have totally different features or partly different features from each other, the doctor operating on the report edit screen 44 can decide to add another plain page of lesion describing template 60 or copy the edited page of lesion describing template 60. On the copied page, the doctor may just reselect those term selection buttons 51 relating to observation items of different features in order to input a comment on the lesions having partly different features, which will save much time as compared to the case of inputting the comment from the beginning.

Because the lesion describing templates 60 are displayed in the form of tabbed panels, these templates 60 may be changed over instantly by selecting the panel tabs, which further facilitates comment entry.

In the above embodiment, merely the selected state of the term selection buttons 51 of the original is reproduced in the copy. Alternatively, the whole state of data entry in the original, including information input in the entry boxes 61, may be reproduced in the copy.

Figure 10:
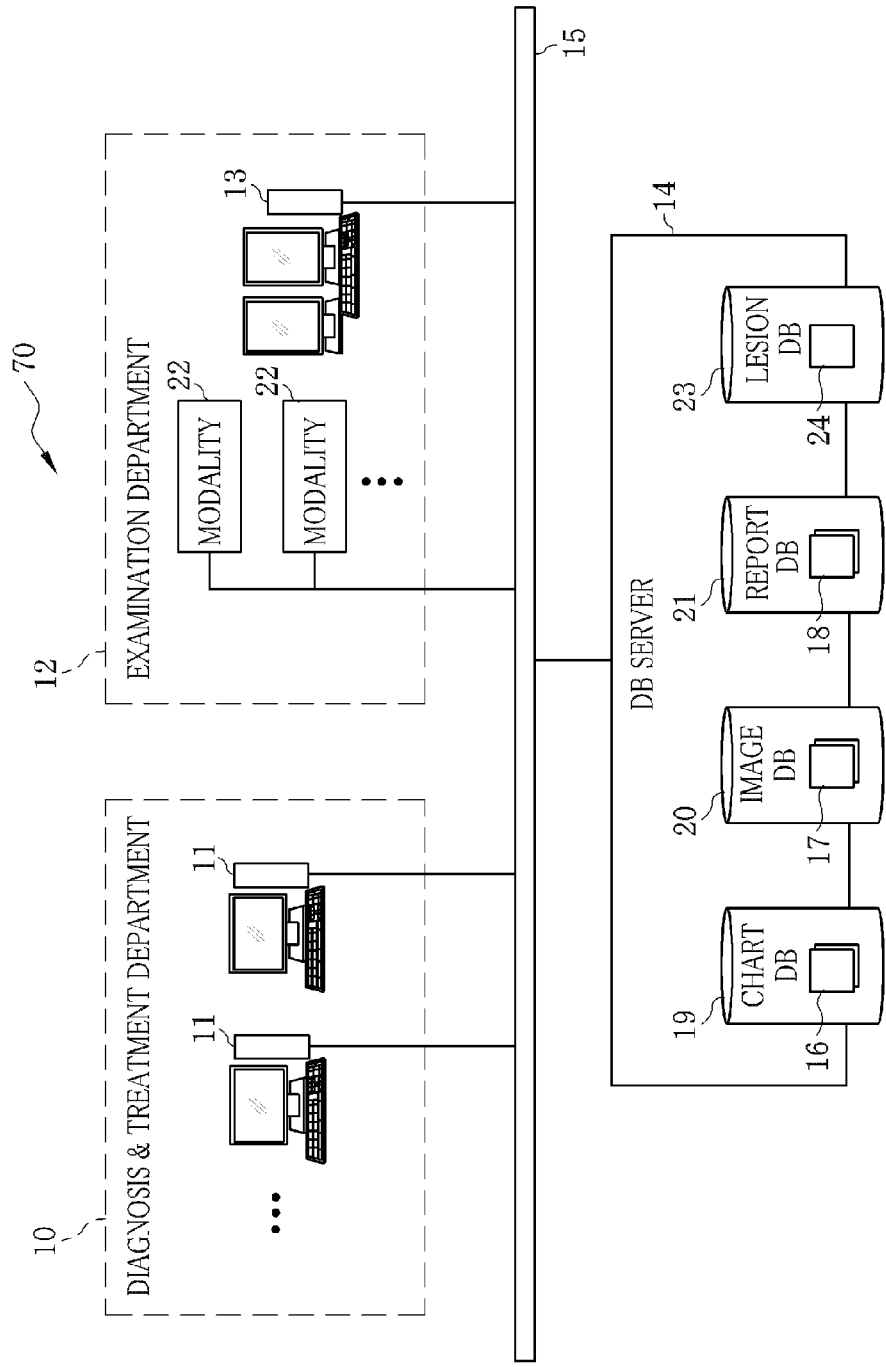
FIG. 10 is a diagram illustrating another structure of a medical information system according to another embodiment.

Referring now to FIG. 10, a medical information system 70 according to another embodiment of the present invention is illustrated, which has basically the same structure as the first embodiment of FIG. 1. Equivalent components are designated by the same reference numerals as in the first embodiment, and merely essential features to the second embodiment will be described hereinafter.

Like the first embodiment, terminals 11 and 13 and a database server 14 of the medical information system 70 are each embodied by installing control programs and applications such as a report editing client program in a basic computing device. The basic computing devices may have the same basic structure as shown in FIG. 2, consisting of a CPU 30, a memory 31, a storage device 32, a LAN port 33, and a console 34, which are connected to each other through a data bus 35.

Figure 11:
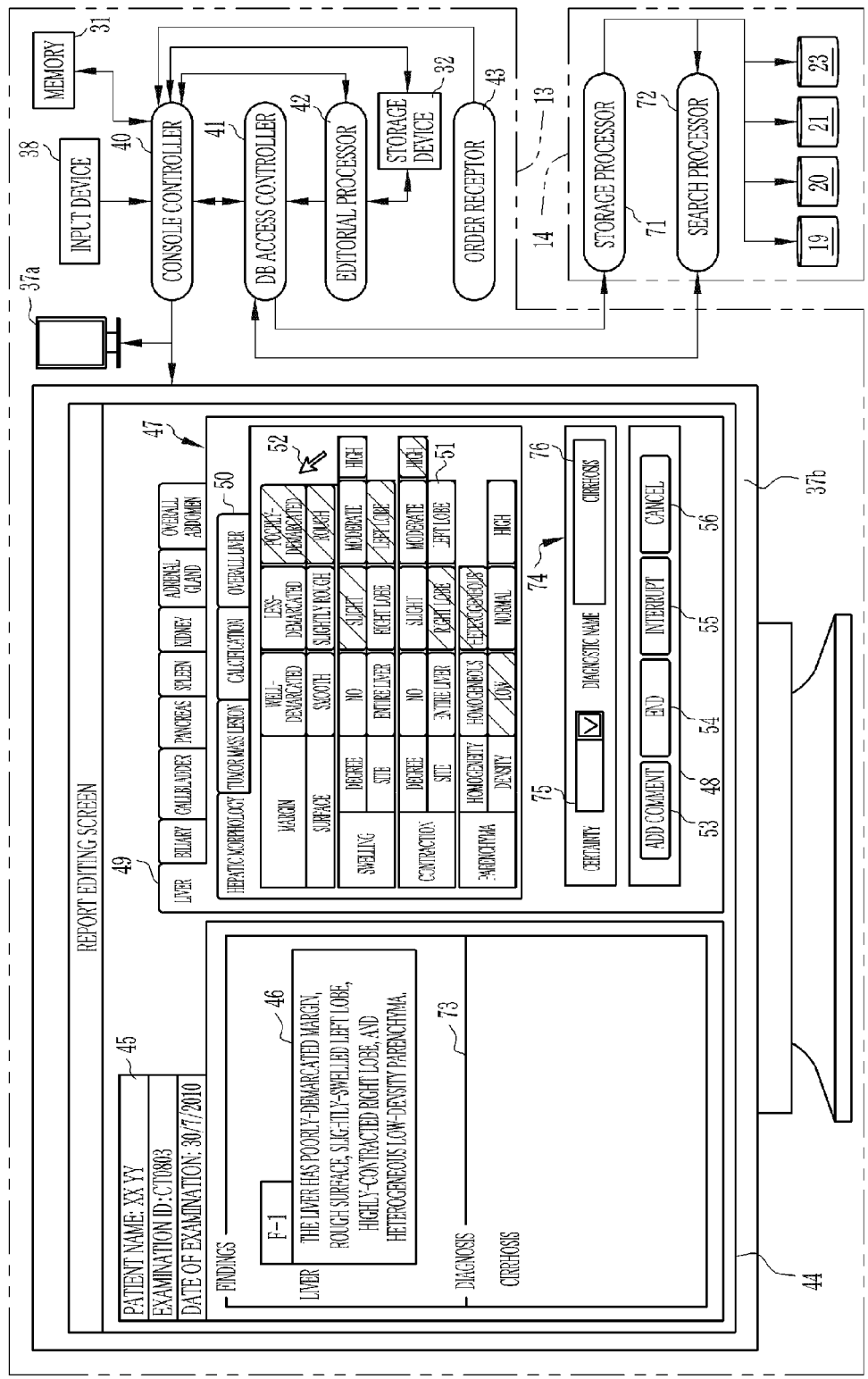
FIG. 11 is a diagram illustrating a schematic structure of a report creation terminal and an example of a report editing screen of the embodiment of FIG. 10.

Referring to FIG. 11, the CPU 30 of the report creation terminal 13 functions as a console controller 40 (corresponding to a display controller), a database access controller 41, an editorial processor 42, and an order acceptor 43, when the report editing client program is activated.

In the medical information system 70, the database server 14 includes a lesion database 23 that stores data of lesions extracted from data of many reports 18 in the form of a lesion data table 24 (see FIG. 18), wherein the lesion data are sorted according to patients. Moreover, each report 18 is given a report ID, so that data of the stored reports 18 may be retrieved using any of report ID, examination ID, patient ID, patient name and other factors as search keys.

Thus, on a report creation terminal 13 in an examination department 12, a doctor in charge of radiographic interpretation may refer to past medical reports 18 relating to a particular patient and may create a new report 18 on the same patient on the basis of a copy of the previous report 18, for example, for use in checking therapeutic efficacy on the patient in the follow-up of this patient.

As shown in FIG. 11, the database server 14 includes a CPU that functions as a storage processor 71 and a search processor 72. A report editing screen 44 is provided with a diagnosis display area 73 and a diagnosis input area 74 in addition to a basic information display area 45, a comment input area 46, a selective term input area 47 having term selection buttons 51, and an operation button area 48 having operation buttons 53 to 56.

In the diagnosis input area 74, a pull-down menu box 75 for inputting the degree of certainty of the diagnosis and an entry box 76 for inputting diagnostic name of disease are provided in the second embodiment. When an inverted triangle beside the pull-down menu box 75 is clicked on, options indicating different degrees of certainty, e.g. high, middle and low, or predicable and suspicious, are displayed as the pull-down menu. The diagnostic name written in the diagnostic name entry box 76 is also displayed in the diagnosis display area 73. In the example of FIG. 11, "cirrhosis" is input in the diagnosis input area 74 and displayed in the diagnosis display area 73.

Figure 12:
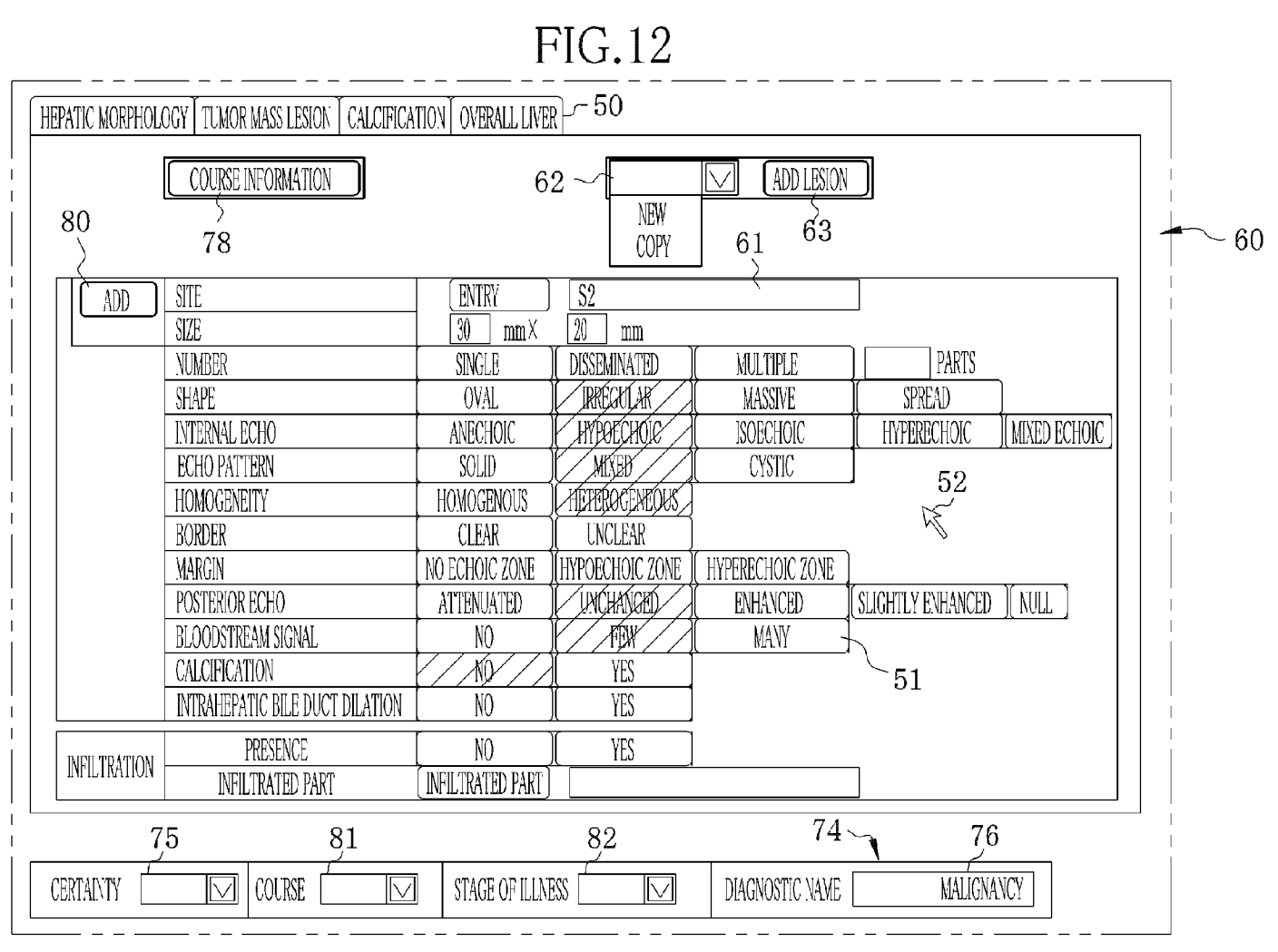

As shown in FIG. 12, a lesion describing template 60, which may be opened by selecting a tab "tumor mass lesion" of small classification panels 50 in the selective term input area 47, has term selection buttons 51, entry boxes 61, a pull-down menu box 62 and a lesion addition button 63. Like the first embodiment, the pull-down menu box 62 and the lesion addition button 63 are operated to designate adding a new template panel 60 or copying an edited template 60 in the same manner as described in the first embodiment. The lesion describing template 60 further has a diagnosis input area 74, a course information button 78 and an add button 80 in the second embodiment. The diagnosis input area 74 of the lesion describing template 60 is provided with a pull-down menu box 81 for inputting the course of illness, and a pull-down menu box 82 for inputting the stage of illness in addition to the pull-down menu box 75 for inputting the degree of certainty and the diagnostic name entry box 76.

Although the lesion describing template 60 is provided for reporting a tumor mass lesion, a similar template may be provided for reporting other kinds of lesions, e.g. hemorrhagic lesions such as intracerebral hemorrhage or subarachnoid hemorrhage. In that case, the lesion describing template does not necessarily have the pull-down menu box 82 for inputting the stage of illness, as implied in connection to those lesions diagnosed as intracerebral hemorrhage in the lesion data table 24 in FIG. 16. Note that the function of the course information button 78 will be described in detail later.

Figure 13:
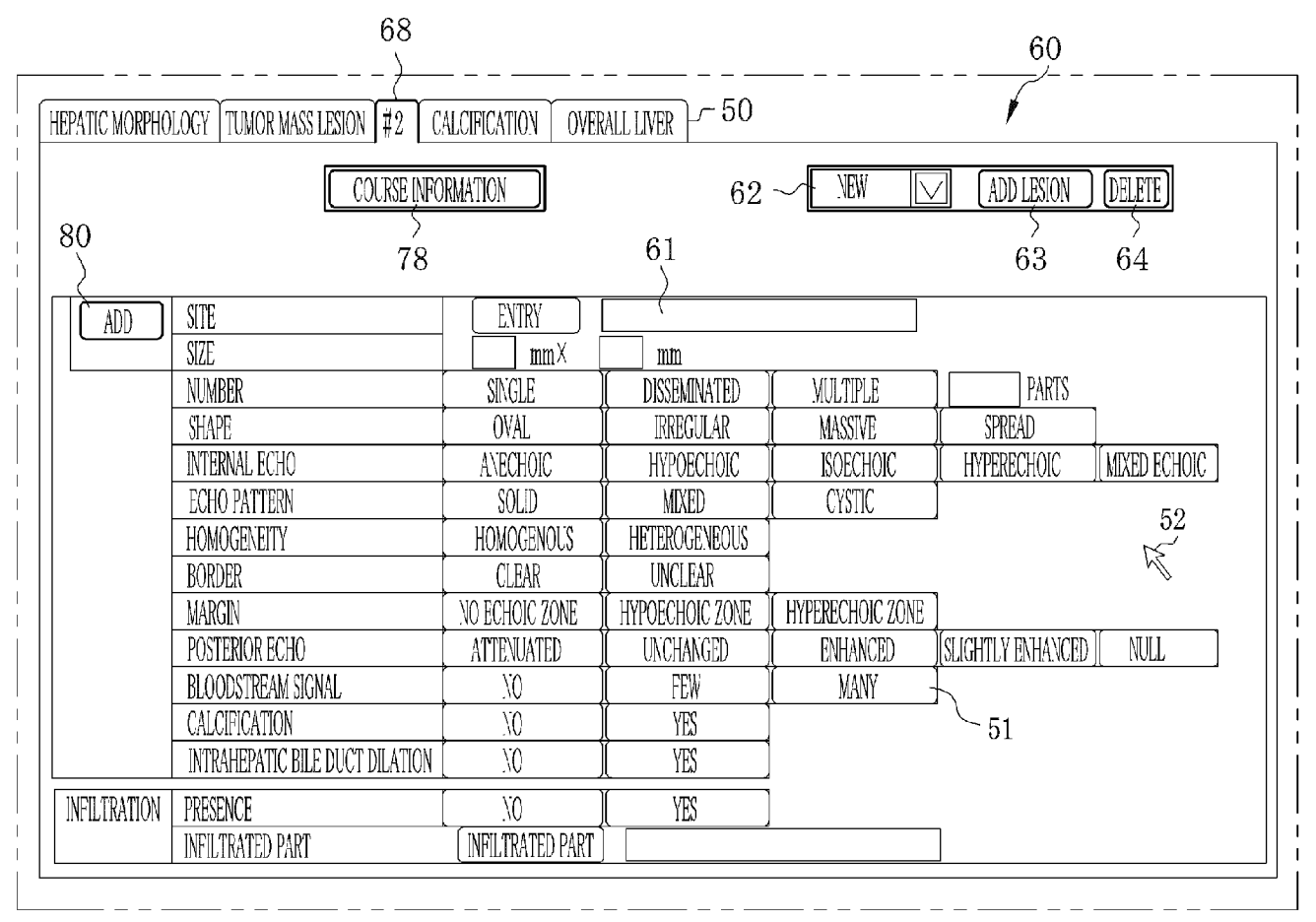

The add button 80 is for adding entry boxes 61 for observation items "site" and "size" on the lesion describing template 60. When the add button 80 is clicked on, another set of entry boxes 61b for "site" and "size" are provided below default entry boxes 61a for "site" and "size", as shown in FIG. 13. However, it is possible to provide such an add button for another observation item, e.g. "shape".

When multiple lesions are found in a series of examination images 17 and these lesions have totally different features, e.g. some being solid tumor mass lesions whereas other being cystic tumor mass lesions, a radiographic interpreting doctor may select the option "add-new" in the pull-down menu 62 of the lesion describing template 60, and then click on the lesion addition button 63. Then a plain page of lesion describing template 60 appears as an additional tab panel 68 in the selective term input area 47 on the report editing screen 44, as shown in FIG. 13.

When multiple lesions found in a series of examination images 17 have partly different features from each other, the doctor may select the option "copy" in the pull-down menu 62 and then click on the lesion addition button 63. Then a copy of the previous page of the lesion describing template 60 appears as an additional tab panel 69, as shown in FIG. 14, where some of the term selection buttons 51 have been automatically selected on the basis of selective input data representative of the selected state of the term selection buttons 51 on the previous template page, the selective input data being stored as temporary data in the memory 31.

When multiple lesions of different sizes are found in different sites but other features of these lesions are substantially identical, the doctor may operate the add button 80. Then another set of item entry boxes 61b for "site" and "size" are provided as an additional item 84 below the default item entry boxes 61a, as shown in FIG. 15. The additional item 84 is provided with a delete button 85 for canceling this additional item 84.

A sentence or comment produced using the lesion describing template 60 is stored in association with a lesion ID for identifying each lesion described by this sentence. When an additional template page or tab 68 or 69 is opened by operating the lesion addition button 63 after selecting "new" or "copy" on the pull-down menu 62, or when the add button 80 is operated to add an additional item 84, another comment input area 46 is automatically added to, and a different lesion ID is given to a comment written in the additional comment input area 46.

Figure 16:
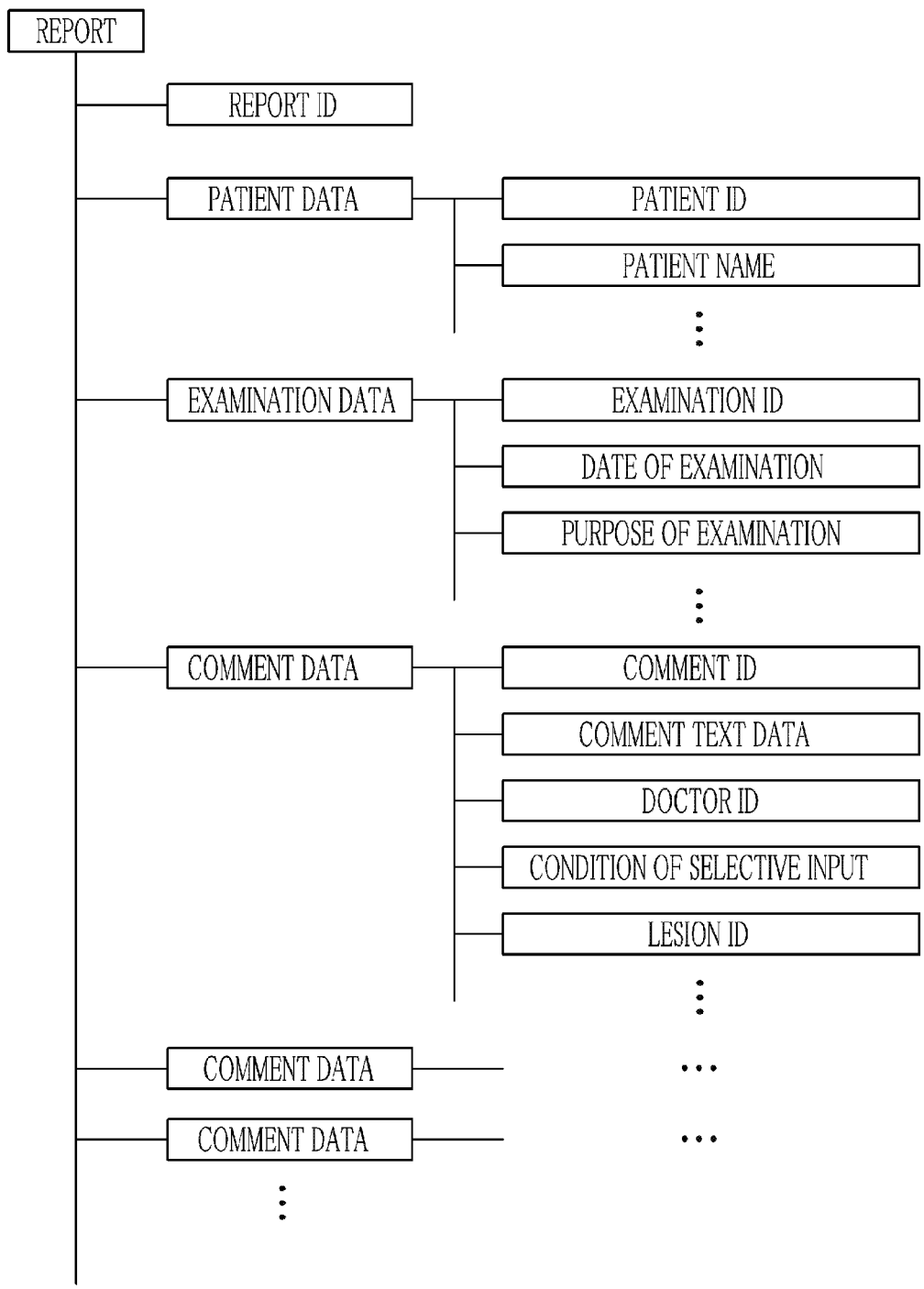
FIG. 16 is an explanatory diagram illustrating a data structure of a medical report.

Referring to FIG. 16, the data structure of one report 18 is illustrated. The report 18 contains patient data such as a patient ID and a patient name, examination data such as an examination ID, the date of examination and the purpose of examination, and comment data. The comment data includes a comment ID, comment text data, a doctor ID and the selective input data entered through the template 60. In addition to these data components, at least a lesion ID is included in the comment data if it is produced on one lesion describing template 60. The report 18 may further contain image IDs of those examination images observed for creating the report 18 and other information indicated in the order for the corresponding examination.

Figure 17:
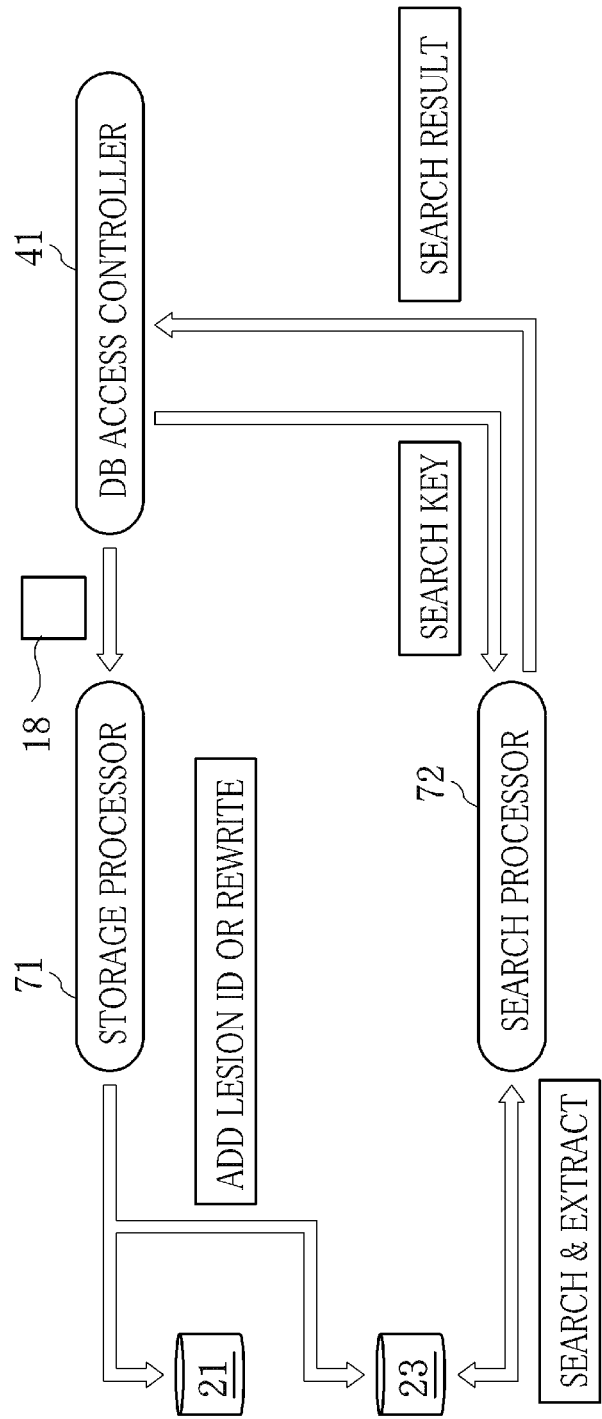
FIG. 17 is an explanatory diagram illustrating the operation for storing lesion data in a lesion data table or retrieving course information on a lesion from the lesion data table.

As shown in FIG. 17, the lesion ID is issued from the storage processor 71 of the database server 14. The storage processor 71 stores data of each report 18 in a report database 21 as the data is sent with the storage command from a database access controller 41 of the report creation terminal 13. If any comment data in the report 18 as produced on the lesion describing template 60 does not yet have any lesion ID, that is, when the report 18 is newly created one or when a comment on a lesion is added to the report 18 using a newly-added or copied tab 68 or 69 or an additional observation item 84, the storage processor 71 issues a new lesion ID and adds it to the comment data.

On the other hand, when a past or previous report 18 on the same lesion of the same patient is copied to reuse it for creating a report 18 on an examination of the same patient for the follow-up examination on the same lesion, the storage processor 71 does not issue a new lesion ID but gives the same lesion ID as used in the original report 18 to comment data of the copied report 18.

The storage processor 71 extracts the report ID, the patient ID, the date of examination, the selective input data entered through the lesion describing template 60, the diagnostic name, the course, the stage of illness, the lesion ID and other data from the data of each report 18, to register the extracted data in the lesion data table 24 stored in the lesion database 23. As shown in FIG. 18, the lesion data table 24 has items for the extracted data such as lesion ID, state of selective data entry, diagnostic name, course, stage of illness, report ID, date of examination. These items are sorted by the patient ID, i.e. grouped according to the patients. From this lesion data table 24, medical history of a patient, including the individual course of illness of the patient, is available.

For example, the table 24 shows that a lesion with a lesion ID "00001" of a patient ID with a patient ID "01234" is first detected by an examination on Jul. 30, 2010, and a comment on this lesion is written in a report 18 with a report ID "01524", wherein the selective input data for this comment includes "site: S2", "size: 30 mm×20 mm", "shape: irregular", "internal echo: hypoechoic", and etc.; the diagnostic name is "malignancy"; and the stage of illness is "I". As for the first detected lesion, no data is registered in the item of the course of illness.

The lesion identified with the ID "00001" was observed in the follow-up examinations, and information obtained from these examinations is registered in the following lines to the first line for this lesion in the table 24. In this example, the size of this lesion grew to 34×25 mm and the course was worsen in the first follow-up examination, but the size reduced to 22×15 mm and the course was favorably altered in the second follow-up examination, and the size was unchanged in the third follow-up examination. This lesion stays in "I" stage of illness. On the other hand, a lesion identified with an ID "00002" has disappeared in the second follow-up examination, which indicates that this lesion was healed by medical or surgical treatments.

The lesion with the ID "00002" and a lesion with the ID "00003" are associated with the same report IDs "01680", "01692" and "01715" and the same dates of examination. This means that these two lesions have been detected through the same examinations and reported in the same medical reports 18 using another template page opened by operating the pull-down menu box 62 and the lesion addition button 63 or an additional observation item 84 added to the lesion describing template 60 by operating the add button 80.

When the storage processor 71 issues a new ID to a new lesion of a patient, the storage processor 71 adds a new line for registering the new lesion ID to those lines of the lesion data table 24 which are allocated to the same patient, and fills other data items of the new lesion in this line. If an already issued lesion ID is allocated to a lesion of a patient, the storage processor 71 adds a new line to those lines which are subordinated to this lesion ID, and fills other data items of this lesion in the new line. Accordingly, when a new lesion is detected from a patient, or each time examination data of a lesion is acquired through a follow-up examination of a patient, a new line for registering data of this lesion is added to the lines for this patient in the lesion data table 24. If the lesion is healed through surgical or medical treatment, no more examination data on this lesion will be added to the table 24.

A command to copy and reuse data of a designated past report 18 may be entered through input devices 38 using a patient ID, an examination ID or the like as a search key. This command is transferred via the console controller 40 to the data access controller 41. Then the data access controller 41 sends a search request to the search processor 72 of the data base server 14. The search processor 72 retrieves data of the designated report 18 from the report database 21, and transfers the retrieved data to the database access controller 41. The console controller 40 controls a monitor 37b to display a copied report editing screen 44 that reproduces the previous state of selective data entry in the designated past report 18 on the basis of the selective input data transferred from the search processor 72 and screen rendering data stored in the storage device 32. When a command to create a new report 18 without copying any past report 18 is given to the report creation terminal 13, a plain or default report editing screen 44 is displayed on the monitor 37b, without making data retrieval from the report database 21.

It is also possible to determine whether an order received on the order acceptor 43 is ordering an initial examination or a follow-up examination with reference to data of past orders retrieved using the same patient ID as contained in the received order or other information such as the purpose of the examination, as search keys. If the retrieved data shows that the same patient took an examination under the same condition as designated by the received order, the order is for the follow-up. When the ordered examination is judged to be an initial one, a plain report editing screen 44 for creating a new report 18 may be displayed. When the ordered examination is judged to be a follow-up examination, data of a previous report 18 on the same lesion of the same patient may automatically be retrieved to display a copied report editing screen 44 reproducing the state of selective data entry in the previous report.

The course information button 78 gets active when the previous report 18 on the same lesion of the same patient is copied and reused for the follow-up. When the course information button 78 is clicked on, the console controller 40 sends at least a search key for retrieving information on the course of the lesion to be reported using a copied lesion describing template 60. Specifically, the search key includes one or more lesion IDs attached to the data of the copied report 18.

In FIG. 17, the database access controller 41 sends a search request for the course information with the received search key to the search processor 72 of the database server 14. The search processor 72 searches the lesion data table 24 for the identical lesion ID to the lesion ID given as the search key. Then the search processor 72 extracts data stored in the lines under the identical lesion ID, and produces a course information list 88 from the extracted data, as shown for example in FIG. 19. The course information list 88 is fed as a search result to the database access controller 41.

As shown in FIG. 19, the course information list 88 includes those data items which are extracted from those lines of the lesion data table 24 which are associated with the lesion ID designated by the search key, including the patient ID, the diagnostic name of disease, the course, and the illness stage. The course information list 88 also includes numerical data indicating the selective input data, including the site, the size, and the volume of the lesion. The course information list 88 shown in FIG. 19A will be produced from the lesion data table 24 of FIG. 18 when the lesion ID "00001" is designated as the search key. The course information list 88 shown in FIG. 19B will be produced from the lesion data table 24 of FIG. 18 when the lesion IDs "00002" and "00003" are designated as the search keys. Since the lesion IDs "00002" and "00003" identify those lesions which have been detected through the same examinations and described on the same reports, these lesion IDs are combined with each other and sent as a pair of search keys. Although it is not illustrated in the drawings, the course information list 88 may further include report IDs and image IDs of key images that are traceable from the report IDs.

The database access controller 41 transfers the course information list 88 from the search processor 72 to the console controller 40. Then the console controller 40 controls the monitor 37b to display the course information list 88 as it is or after processing it, e.g. modifying its layout appropriately.

An example of a modified display style of the course information list 88 is shown in FIG. 20, wherein the patient ID "01234" and the lesion IDs "00002" and "00003" are designated as the search keys, like the example of FIG. 19B. In the example of FIG. 18, thumbnails of key images, changes in volume of the lesion, and the diagnostic name are displayed as the course information segmented by the date of examination. The thumbnails of the key images are retrieved from an image database 20 using the image IDs contained in the course information list 88 as search keys. The changes in volume are presented in numerical values and line charts. The numerical values are standardized to be the maximum volume of the lesion measured at each examination. The line chart is made by plotting the respective numerical values of the volume along the ordinate on an appropriate scale. In this example, the diagnostic name and the line charts are displayed on the common screen with respect to the two lesions with the IDs "00002" and "00003". However, the diagnostic name and the line chart may be displayed separately for each of these lesions, e.g. in parallel to each other on the same screen or in an alternative fashion.

Figure 21:
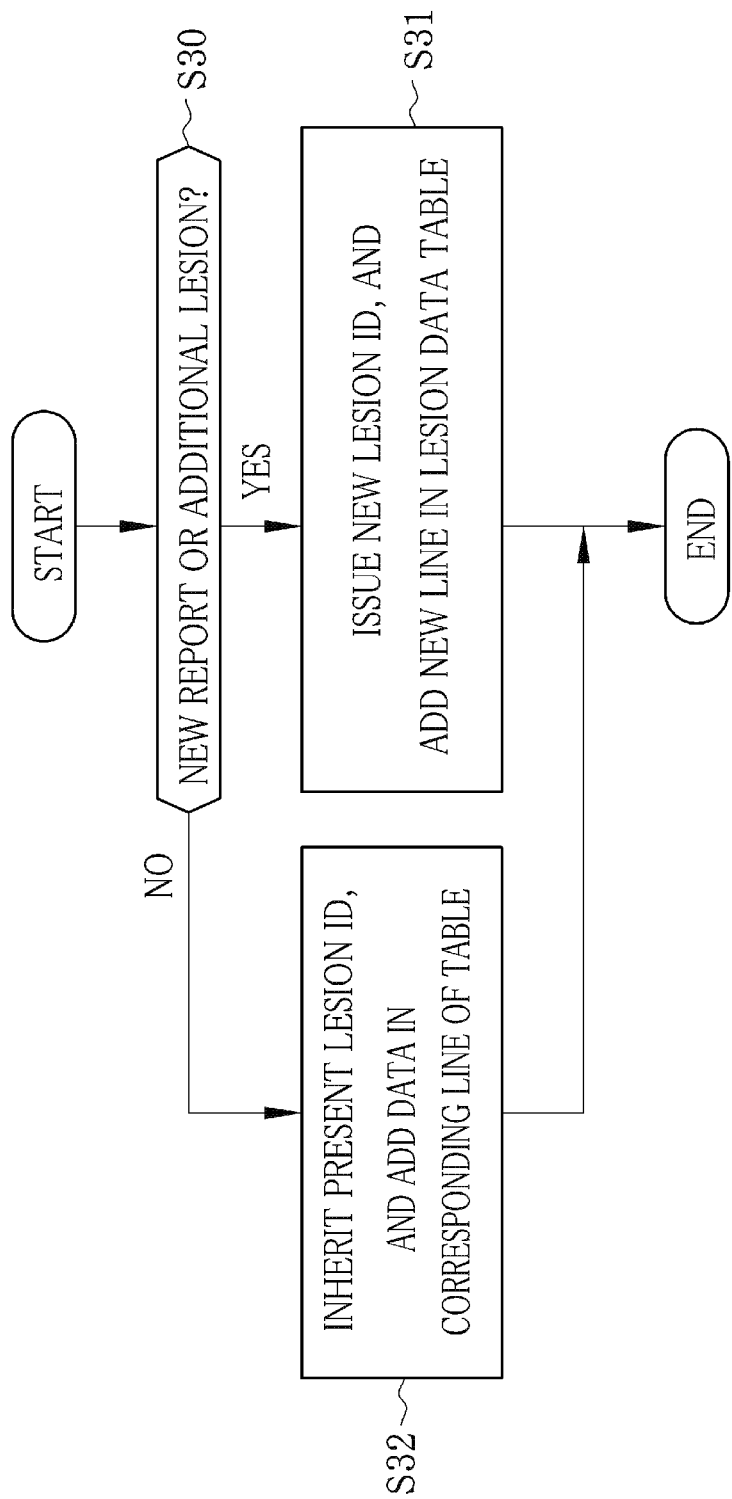
FIG. 21 a flowchart illustrating a sequence of storing lesion data in the lesion data table.

Now the operation of the second embodiment will be described with reference to the flowcharts of FIGS. 20 and 21.

The main sequence from the order for an examination to the creation of a medical report on the result of the examination may be equal to the sequence as described above with reference to FIG. 8 in the first embodiment.

On saving data of a report 18 in the report database 21, if the report 18 is newly created one or a comment on a newly detected lesion is added to the report 18 using an additional tab 68 or 69 or an additional observation item 84 ("yes" in step S30), the storage processor 71 issues a new lesion ID and attaches it to comment data of the new report 18 or to the newly added comment data. Also a new line is appropriately added to the lesion data table 24 in association with the new lesion ID, and the respective data items of the report 18 are registered in this line (step S31).

If a past report is copied and reused for creating a second report 18 ("no" in step S30) on the same lesion of the same patient, a lesion ID already allocated to this lesion is used in the second report. Respective data items describing the lesion on the second report are registered in a line added to the lines with that lesion ID in the lesion data table 24 (step S32).

When the report 18 is complete, the report creation terminal 13 sends a notice of completion to the terminal 11 of the doctor who requested the report 18. The requester makes an access to the report database 21 through the terminal 11, to read out the report 18 on the basis of the address of the report 18 that is indicated in the notice of completion. Then a report display screen displaying the report 18 and an image display screen displaying the related examination images 17 to the report 18 appear on the monitors 37 of the terminal 11, allowing the requester to read and check the contents of the report 18.

Figure 22:
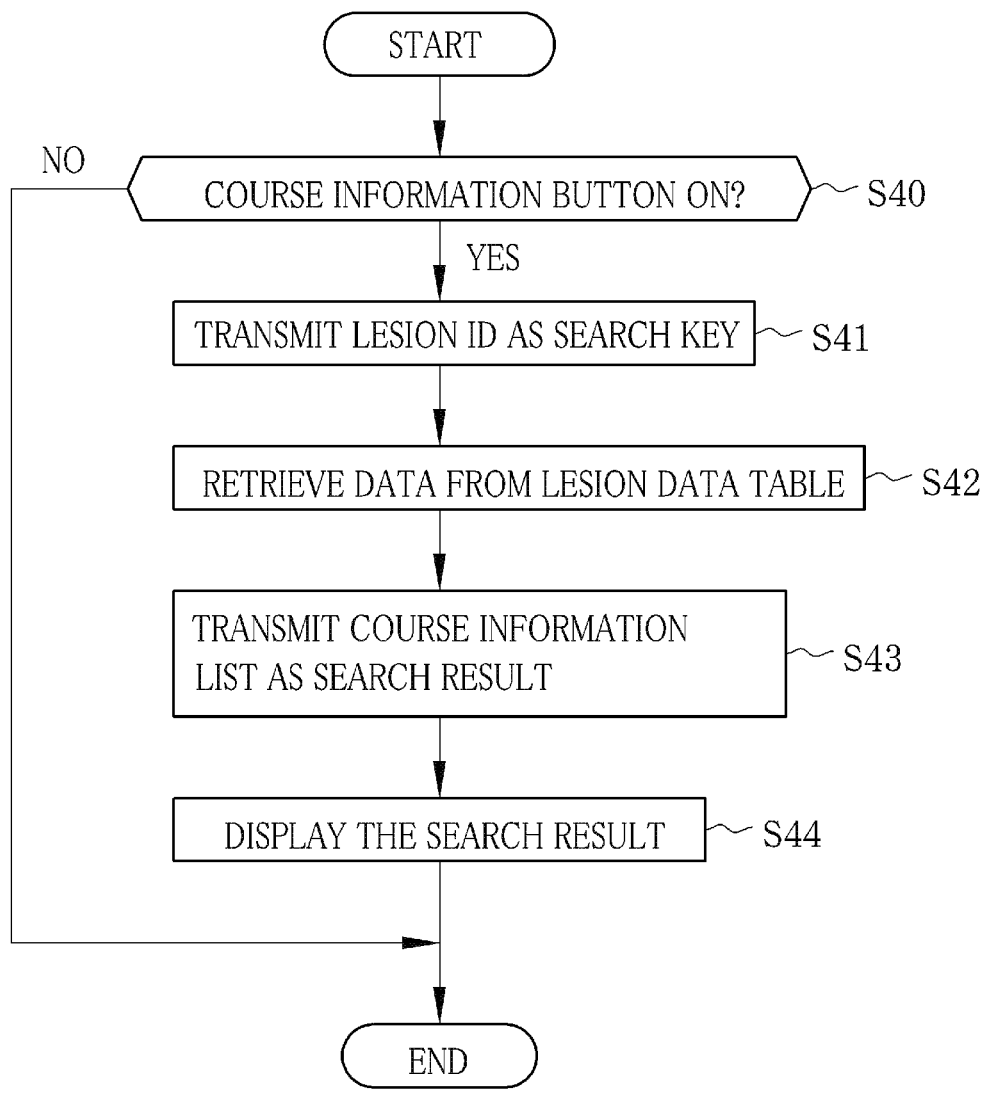
FIG. 22 is a flowchart illustrating a sequence of retrieving course information on a lesion.

When the course information button 78 is operated on a lesion describing template 60 that is a copy of the previous report 18 ("yes" in step S40 of the flowchart of FIG. 22), the console controller 40 transmits a lesion ID as a search key to the database access controller 41, and the database access controller 41 transmits a search request for course information in association with the search key to the search processor 72 (step S41).

Then the search processor 72 extracts data items corresponding to the lesion ID given as the search key from the lesion data table 24 (step S42), and a course information list 88 is produced from the extracted data items, and is transmitted as a search result to the database access controller 41 (step S43).

The course information list 88 received on the database access controller 41 is transferred to the console controller 40. On the basis of the received course information list 88, the console controller 40 controls displaying thumbnails of key images and/or line charts on the monitor 37*b* (step S44).

As described so far, the medical information system 70 of the second embodiment stores and manages the selective input data on each lesion describing template 60 while grouping data items by lesions of the same patient. As compared to the prior art where numerical values or phrases are extracted from comment sentences, the method of the present invention will boost accuracy of extraction of desired course information. The present invention does not need any special analysis such as morphological analysis, but may reflect the selective input data and other data items such as diagnostic name directly on the course information. Therefore, the present invention will guarantee the adequacy and reliability of the retrieved course information.

Using such a lesion ID that is uniquely allocated to each individual lesion as the search key, the retrieved course information entirely relates to the same lesion that is identified with the lesion ID given as the search key. Therefore, the doctor in charge of radiographic interpretation can use the retrieved course information as authentic reference for creating a report on this lesion.

Instead of using a lesion ID as a search key for retrieving course information on the same lesion of the same patient, it may also be possible to use the selective input data as a search key. Thus those reports having data of the same state of selective data entry, i.e. course data of similar lesion of other patients, may be retrieved and displayed for reference.

In an embodiment that allows using the selective input data as a search key, a pull-down menu is provided beside the course information button 78, for choosing either the search for course information on the same lesion of the same patient or the search for course information on similar lesions of other patients. After selecting some of the term selection buttons 51 and inputting data in the data entry boxes 61, the doctor may choose the search for course information on similar lesion of other patient and then click on the course information button 78. Then, using data of the selective data entry state as a search key, the search processor 72 of the database server 14 searches the lesion data table 24. In that case, data on the lesion of the patient in question is excluded from the search targets. In a case where a numerical value such as the volume or size is included in the search key, it is possible to use a wider range of the numerical value as the search key. It is also possible to narrow the search range. For example, the search targets may be limited to those examination data acquired in the nearest preceding month, or those cases indicating good progress.

In that case, the search processor 72 makes a list of course information from the search result in the same way as described above, and transmits the list to the database access controller 41. Then the console controller 40 controls the monitor 37*b* to display the course information on the similar lesions of other patient on the basis of the received course information list.

In a case where cerebral hemorrhage was found at an initial examination on a patient, for instance, the doctor in charge of radiographic interpretation may input data on the cerebral hemorrhage in a template for reporting hemorrhagic lesion, which is not shown but may have a similar structure as the template 60. If for example the hemorrhagic lesion is set on putamen, has a volume of 3.2 cc, and is isodense, the doctor inputs these data items on the template.

Thereafter when the course information button 78 is clicked on, the database access controller 41 sends the search processor 72 a search request with search keys including "site: putamen", "volume: 3.0-3.5 cc" and "density: isodense". Then the search processor 72 extracts data of those lesions hit by these search keys from among data of lesions registered in the lesion data table 24. The search processor 72 produces a course information list from the extracted data, and sends it back to the database access controller 41.

Figure 23:
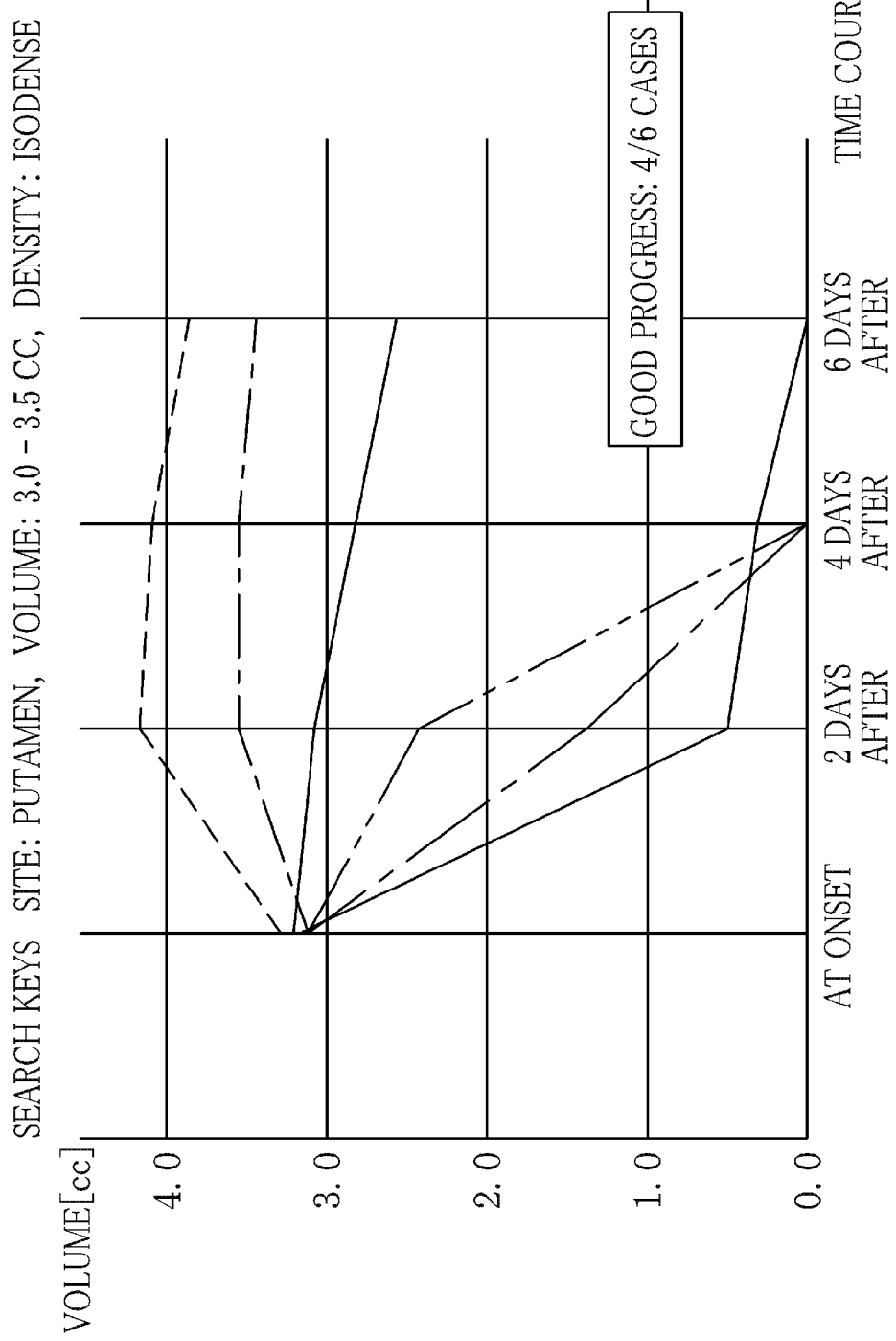
FIG. 23 is a diagram illustrating an example of displaying course information on similar lesions of other patients in a graph.

An example of a course information display screen is shown in FIG. 23. In this example, transitions in volume of cerebral hemorrhages of other six patients are illustrated by line charts in the time course from the onset time or initial time of detection. In addition, information about how many cases show good progress among all. It is also possible to provide the course information display screen with links to such medical chart data or report data that relate to cases showing good progress. Also when the selective input data or the state of selective data entry on the template is used as the search key, adequacy and reliability of the retrieved course information on the lesion are guaranteed. Providing course information on similar lesions of other patients, especially on cases showing high therapeutic efficacy, will help the doctor make a plan for treatments.

In the above embodiment, course information relating to a designated lesion is provided on the report creation terminal 13. Such course information may also be provided on the terminal 11 of the diagnosis and treatment department 12, so that the doctor who requested a report 18 may refer to the course information in combination with the report 18. In that case, a display screen of the terminal 11 should preferably be provided with an entry box for inputting search keys, such as a lesion ID or other data items, to send a search request to the database server 14 and get the search result on the terminal 11 in the same way as described above with respect to the report creation terminal 13. Alternatively, the course information list may be automatically sent to the terminal 11 together with the notice of completion of the report 18. Providing the requesting doctor with the course information relating to the reported lesion can facilitate getting informed-consent from the patient. The course information may help planning therapeutic program.

Figure 24:
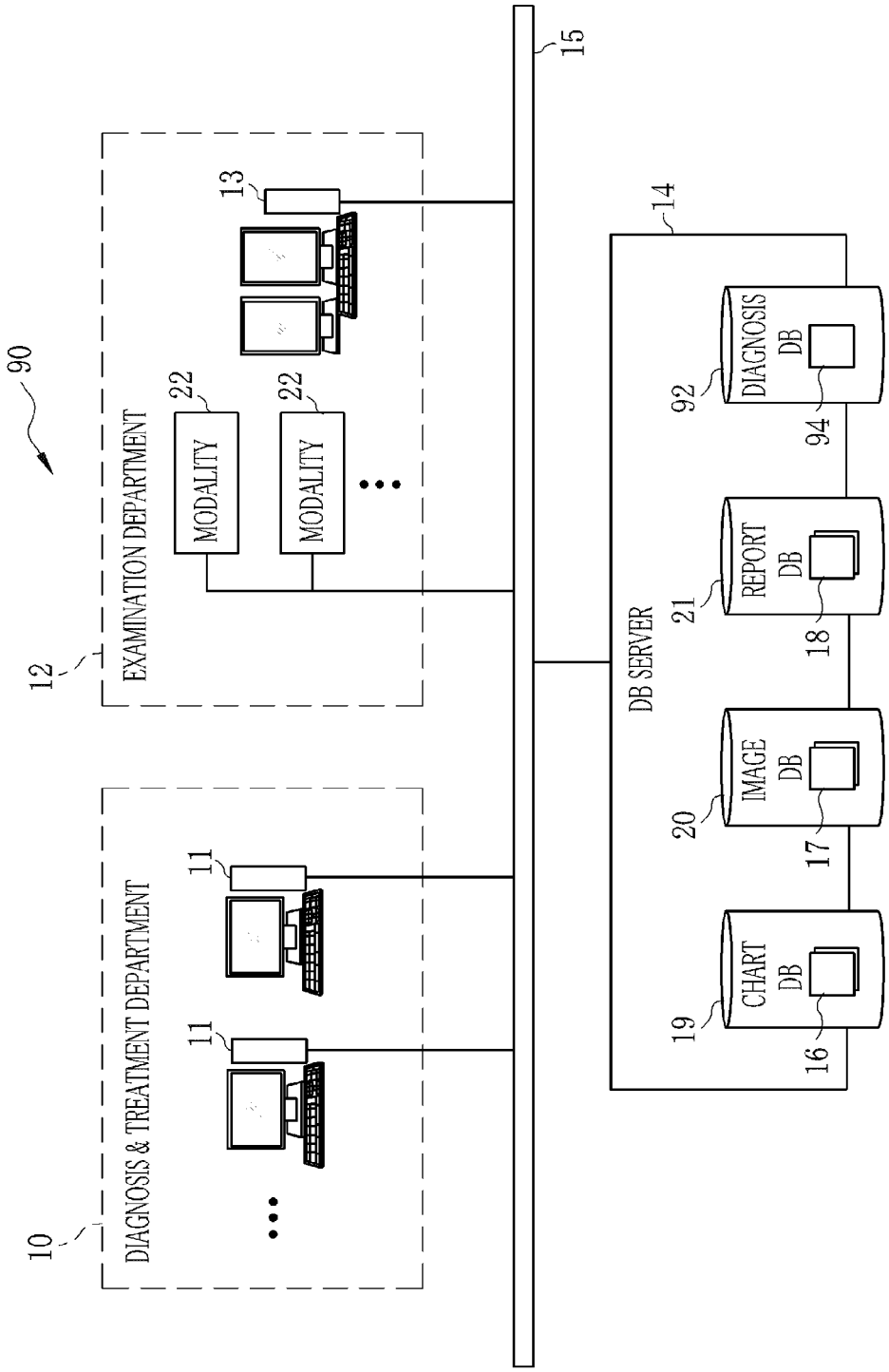
FIG. 24 is a diagram illustrating another structure of a medical information system according to another embodiment.

A medical information system 90 according to another embodiment of the present invention will now be described. As shown in FIG. 24, the medical information system 90 includes a diagnosis database 92 in a database server 14. The diagnosis database 92 stores diagnostic data table 94 (see FIG. 28) containing data of diagnoses extracted from data of medical reports 18 that have been created on report creation terminals 13. The medical information system 90 has basically the same structure as the above described medical information systems 2 and 70. Equivalent components are designated by the same reference numerals as in the above embodiments, so that the following description merely relates to essential features to the present embodiment.

Like the first embodiment, terminals 11 and 13 and a database server 14 of the medical information system 70 are each embodied by installing control programs and applications such as a report editing client program in a basic computing device. The basic computing devices may have the same basic structure as shown in FIG. 2, consisting of a CPU 30, a memory 31, a storage device 32, a LAN port 33, and a console 34, which are connected to each other through a data bus 35.

Figure 25:
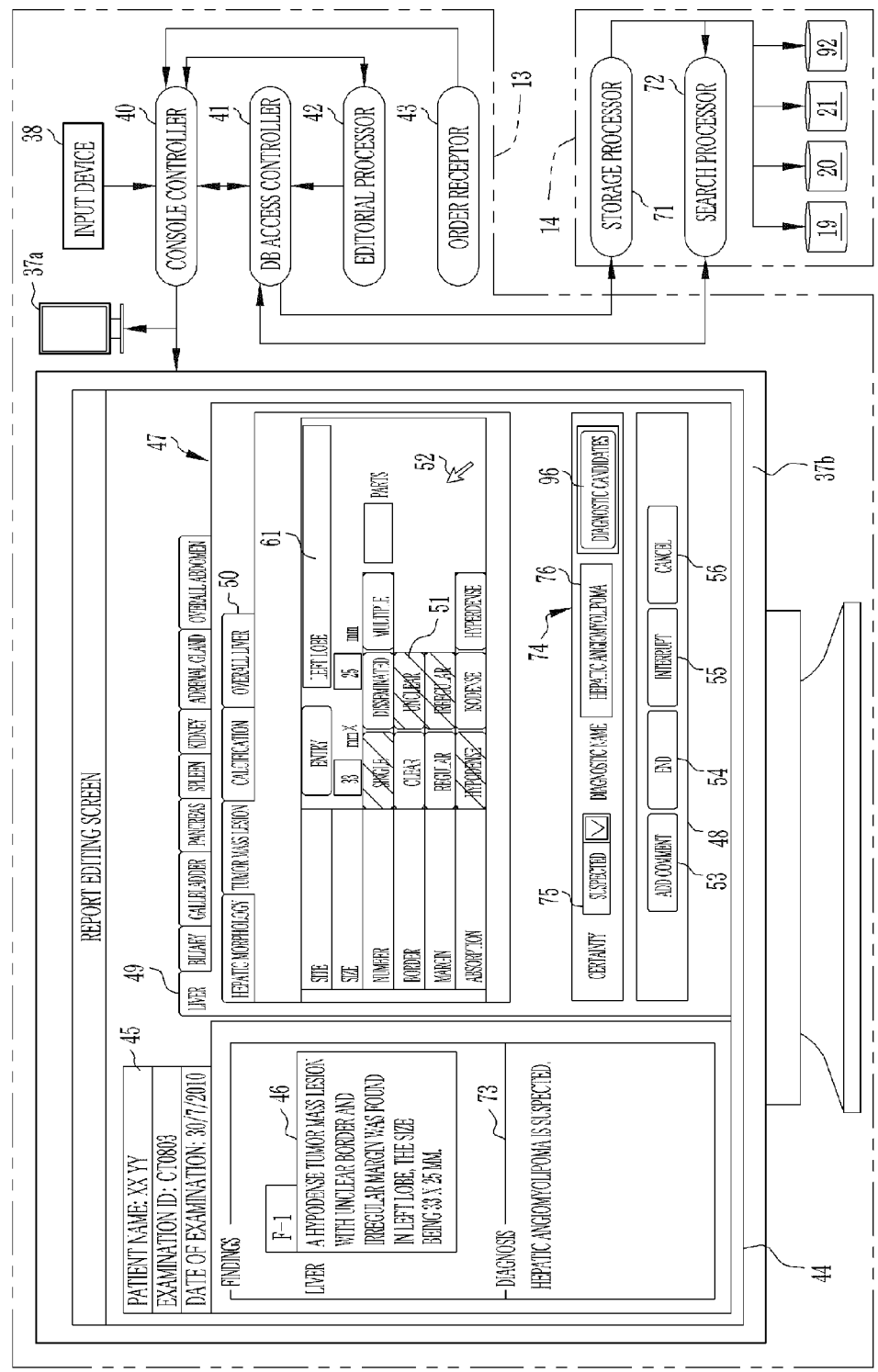
FIG. 25 is a diagram illustrating a schematic structure of a report creation terminal and an example of a report editing screen of the embodiment of FIG. 24.

Referring to FIG. 25, the CPU 30 of the report creation terminal 13 functions as a console controller 40 (corresponding to a display controller), a database access controller 41, an editorial processor 42, and an order acceptor 43, when the report editing client program is activated.

When the report editing client program is activate, a report editing screen 44 appears on a monitor 37b. An example of the report editing screen 44 is shown in FIG. 25, wherein a selective term input area 47 for reporting a tumor mas lesion is opened by selecting a tab "liver" of large classification panels 49 and then a tab "tumor mass lesion" of small classification panels 50.

Each small classification panel 50 is provided with a plurality of term selection buttons 51. On the basis of the terms selected through the term selection buttons 51, a comment is displayed in a comment input area 46. The operator may add some words and phrases to the displayed comment through the keyboard or the like.

In a diagnosis input area 74 of the selective term input area 47, a pull-down menu box 75 for inputting the degree of certainty of the diagnosis, an entry box 76 for inputting diagnostic name of disease, and a button 96 for displaying some diagnostic names as candidates are provided. As described in detail later, when the button 96 is operated, a list of diagnostic names inferred from other data items input in the report 18 is displayed in an appropriate manner. The doctor who is creating a report 18 on the report editing screen 44 may make the diagnosis and input a diagnostic name of disease in the entry box 76 using input devices 38, with reference to the diagnostic names listed as candidates.

When an inverted triangle beside the pull-down menu box 75 is clicked on, options indicating different degrees of certainty, e.g. "definite", "suspected" and "exception", are displayed as the pull-down menu. When the doctor is definite about his or her diagnosis, the doctor may select "definite". When the doctor writes a suspected disease in the diagnostic name entry box 76, "suspected" should be selected on the pull-down menu 75. When the doctor is not sure about the diagnostic name written in the entry box 76, "exception" should be selected on the pull-down menu 75. The diagnostic name written in the diagnostic name entry box 76 is also displayed in a diagnosis display area 73. In the example of FIG. 25, "suspected" is selected on the pull-down menu 75, and "hepatic angiomyolipoma" is written in the entry box 76. As a result, a diagnosis "Hepatic angiomyolipoma is suspected." is displayed in the diagnosis display area 73.

The database access controller 41 transmits requests to the database server 14 according to commands from the console controller 40 and the editorial processor 42, and receives responses from the database server 14. The requests sent to the database server 14 include request for retrieving examination images 17 from an image database 20, request for storing data of complete reports 18 in a report database 21, request for retrieving data of some reports 18 from the report database 21, request for storing data input in the diagnosis input area 74 in the diagnostic data table 94 of the diagnosis database 92, and request for retrieving some diagnostic names as candidates from the diagnostic data table 94.

Figure 26:
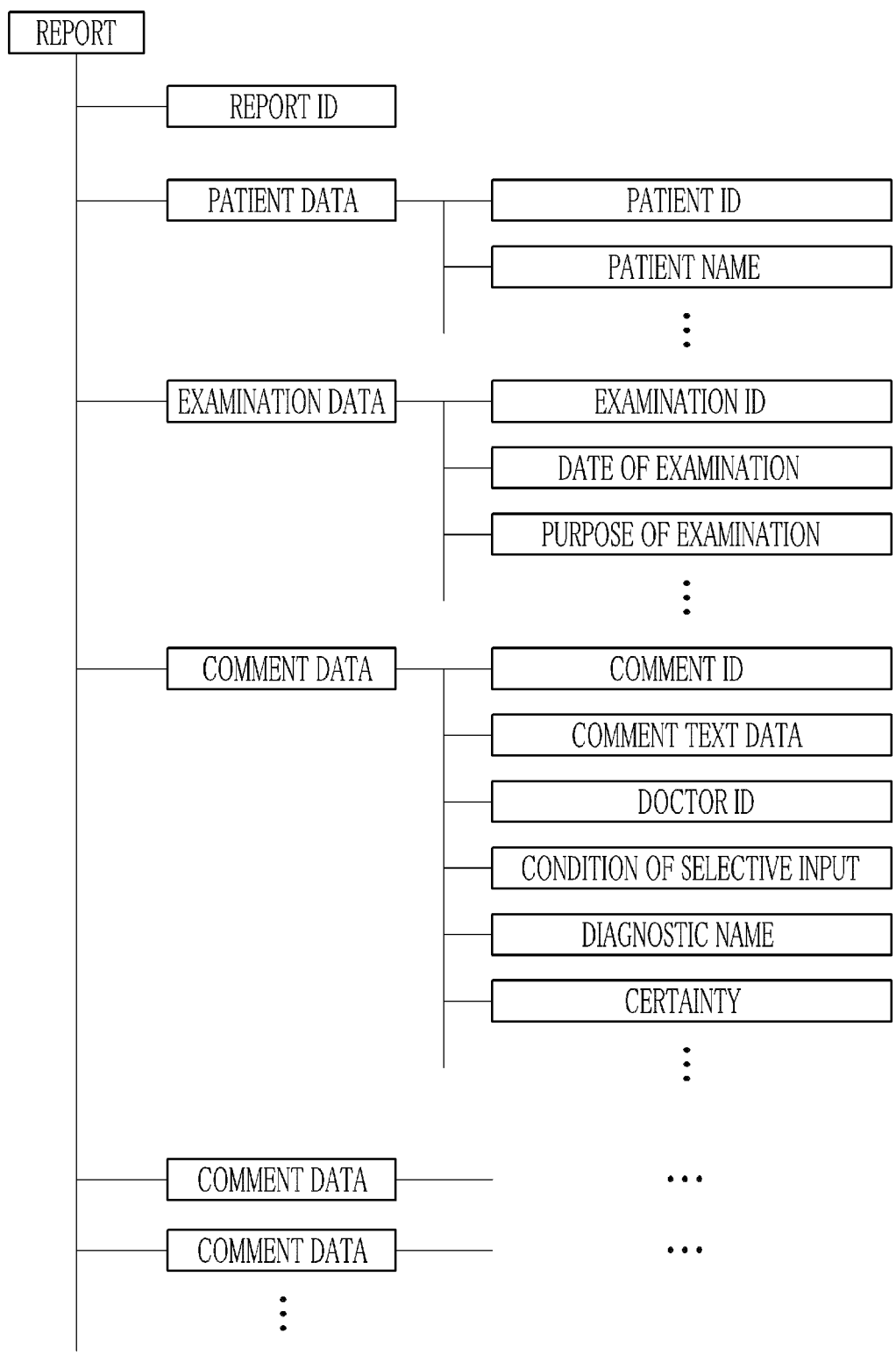
FIG. 26 is an explanatory diagram illustrating a data structure of a medical report according to the embodiment of FIG. 24.

Referring to FIG. 26, the data structure of one report 18 is illustrated. The report 18 contains patient data such as a patient ID and a patient name, examination data such as an examination ID, the date of examination and the purpose of examination, and comment data. The comment data includes a comment ID, comment text data, a doctor ID, the selective input data, the diagnostic name of disease and the degree of certainty. In addition to these data components, the report 18 may further contain image IDs of those examination images observed for creating the report 18 and other information indicated in the order for the corresponding examination.

Figure 27:
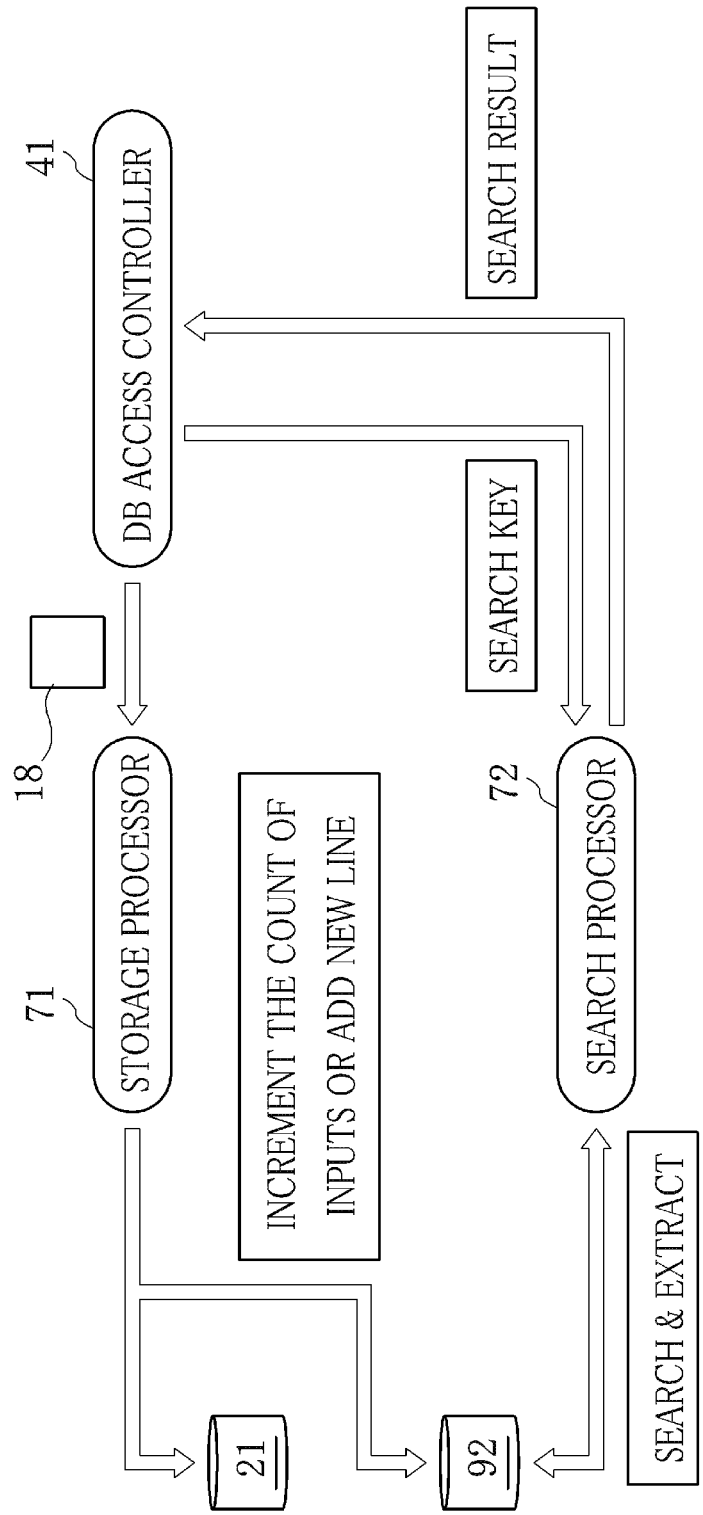
FIG. 27 is an explanatory diagram illustrating the operation for revising a diagnostic data table or retrieving diagnostic names as candidates from the diagnostic data table.

As shown in FIG. 27, the storage processor 71 extracts the selective input data, the diagnostic name and the degree of certainty from among the comment data contained in the report 18 as sent from the database access controller 41 of the report creation terminal 13. On the basis of the extracted data, the storage processor 71 revises the content of the diagnostic data table 94. As shown in FIG. 28, the diagnostic data table 94 has data items including the selective input data, the degree of certainty, the diagnostic name, and the number of input times, i.e. how many times each individual diagnostic name has been written in the reports 18. The diagnostic data table 94 divides these items into large groups by the state of selective data entry, and each large group is subdivided into small groups by the certainty degrees, e.g. "definite", "suspected" and "exception".

Thus the diagnostic data table 94 shows what kinds of diagnoses have been made on what states of selective data entry in the reports along with the frequency of each kind of diagnosis as well as the degree of certainty on the diagnosis. Note that the data items to be registered in the diagnostic data table 94 may not be all data items selectively entered on the report editing screen 44 but may be parts of the entered data items, which may contribute to the diagnosis.

With respect to the example of FIG. 28, in the first state of selective data entry: "number: single", "border: unclear", "margin: irregular", "absorption: hypodense", and "size: maximum length is 30 mm or more, minimum length is 20 mm or more", a diagnostic name "hepatocarcinoma" has been input 20 times at the certainty degree "definite". The diagnostic data table 94 also shows the percentage or ratio of the frequency of the same diagnosis to all diagnoses made under the same condition. In the example of FIG. 28, the ratio of diagnosing as "hepatocarcinoma" at the certainty degree "definite" under the first state of selective data entry is 40% of the entire number of times any diagnoses have been made as definite ones in the similar diagnostic condition. On the other hand, in the same large group, i.e. in the first state of selective data entry, a diagnostic name "hepatic angiomyolipoma" has been input 10 times at the certainty degree "definite". This is 20% of the entire number of times any diagnoses have been made as definite ones in the similar diagnostic condition, i.e. 50 times in this example.

In the small group for the certainty degree "suspected" under the same diagnostic condition, i.e. in the first state of selective data entry, the diagnostic name "hepatocarcinoma" has been input 14 times, and this is 25% of the entire number of times any diagnoses have been made as suspected ones in the first state of selected data entry. As for the certainty degree "suspected" in the first state of selective data entry, the diagnostic name "hepatic angiomyolipoma" has been input 12 times, and this is 21% of the entire number of times. With the certainty degree "exception", the diagnostic name "hepatocarcinoma" has been input 7 times in connection to the first state of selective data entry, and this is 10% of all diagnoses made as exceptions in the first state of selected data entry, and a diagnostic name "hepatic hemangioma" has been input 16 times, and this is 23% of the entire number.

In the same way as above, the diagnostic names, the number of inputs of each diagnostic name and the percentage of the inputs are registered in groups classified by the degree of certainty and in association with a wide variety of combinations of lesion data input as the selective input data in the selective term input area 47 on the report editing screen 44.

The button 96 is operated for displaying some diagnostic names as candidates inferred from the present state of selective data entry in the selective term input area 47. When the button 96 is clicked on, the console controller 40 sends a search request for searching for the diagnostic candidates to the database access controller 41 along with a search key that is specifically the present state of selective data entry in the selective term input area 47, which is temporary stored in the memory 31. As shown in FIG. 27, the database access controller 41 transfers the search request and the search key to the search processor 72 of the database server 14. Then the search processor 72 searches the diagnostic data table 94 for data groups that are subordinated to the corresponding state of selective data entry to the search key, and extracts these data groups as a search result, to send the search result back to the database access controller 41.

Figure 29:
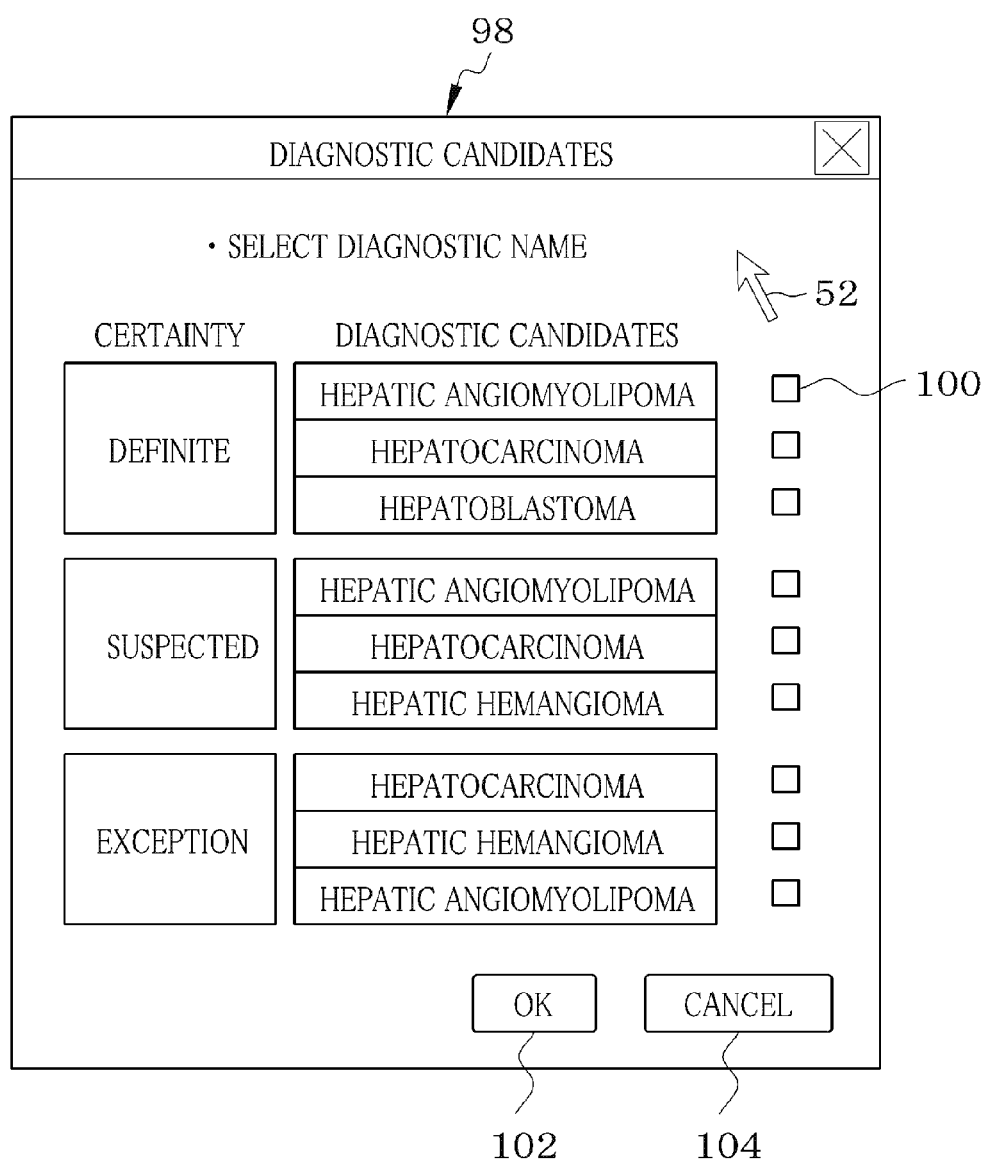
FIG. 29 is an explanatory diagram illustrating an example of a diagnostic candidate display window.

Then the database access controller 41 transfers the search result to the console controller 40 and the console controller 40 produces a diagnostic candidate display window 98 from the search result, as shown for example in FIG. 29. The console controller 40 controls the monitor 37b to display the diagnostic candidate display window as a pop-up window.

In the diagnostic candidate display window 98 of FIG. 29, the diagnostic candidates are listed in groups classified by the degree of certainty. Within each groups, the candidates are named in the order of most frequent or highest percentage of inputs. Check boxes 100 are provided adjacent to the respective diagnostic candidates. The doctor may select one of the candidates on the list by checking its check box 100 and clicking on an OK button 102, depending upon how much the doctor is certain about the selection of the diagnostic name. Then the selected certainty degree and diagnostic name are automatically entered in the pull-down menu box 75 and the diagnostic name entry box 76. If the doctor decides not to select any of the listed candidates, the doctor may click on a cancel button 104 to close the pop-up window 98.

Note that the layout and content of the diagnostic candidate display window 98 are not limited to the illustrated ones, but may be modified appropriately. For example, the number of candidates to be listed at each degree of certainty may be less than or more than three. The diagnostic candidate display window may list only those diagnostic names which have been input more than a predetermined number of times or above a predetermined percent of the time. The number of times each candidate has been input at a particular certainty degree or the corresponding percentage of each candidate may be displayed along with the candidate name. It may be possible to discriminate or highlight those candidate names which have been input more frequently.

The overall operation of the medical information system 90 will be described with reference to the flowcharts of FIGS. 30 to 31. The main sequence from the order for an examination to the creation of a medical report on the result of the examination may be equal to the sequence as described above with reference to FIG. 8 in the first embodiment.

Figure 30:
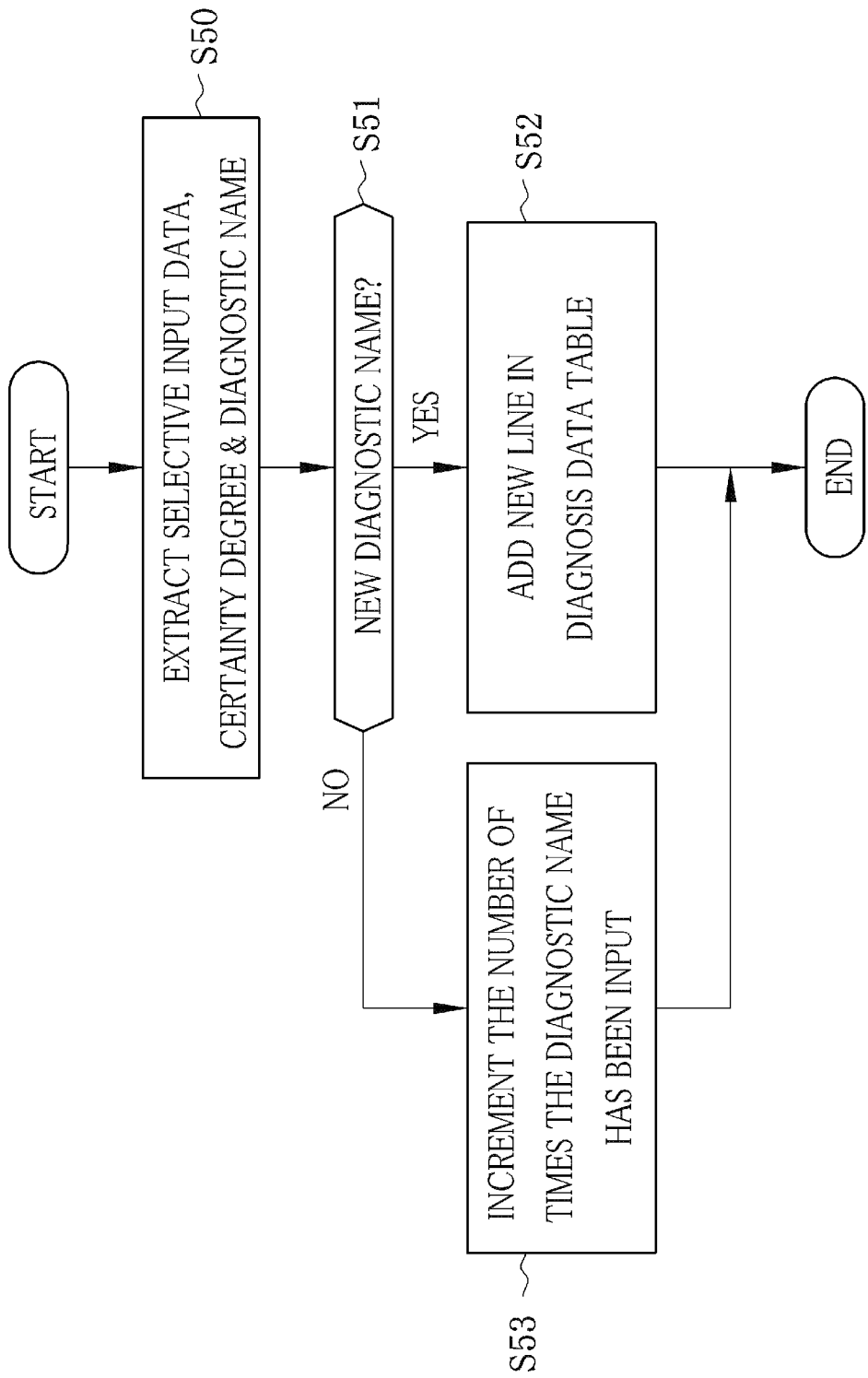
FIG. 30 is a flowchart illustrating a sequence of revising the diagnostic data table.

In the data storage process of the report 18, as shown in FIG. 30, the storage processor 71 extracts the selective input data, the degree of certainty and the input diagnosis name from the report 18 (step S50), and registers the extracted diagnosis name in the diagnostic data table 94 according to the extracted state of selective data entry and degree of certainty. If the input diagnostic name is new, i.e. this diagnostic name has never been input at the same certainty degree under the same state of selective data entry ("yes" in step S51), the storage processor 71 adds a new line for registering this diagnostic name in the group of the same certainty degree within the group corresponding to the selective input data of the report 18 (step S52). At the registration of the diagnostic name, the number of times this diagnostic name has been input at this certainty degree, i.e. "1" for the first time, is also registered. On the other hand, if the input diagnostic name has ever been input at the same certainty degree under the same state of selective data entry ("no" in step S51), the storage processor 71 increments the number of times of the input of this diagnostic name in the corresponding line to the extracted state of selective data entry, the degree of certainty and the diagnosis name (step S53). Each time a diagnostic name is registered under new condition in the diagnostic data table 94, or the number of times of the input of an already registered diagnostic name is incremented, the storage processor 71 recalculates and revises the percentage of input of this diagnostic name in the diagnostic data table 94.

Figure 31:
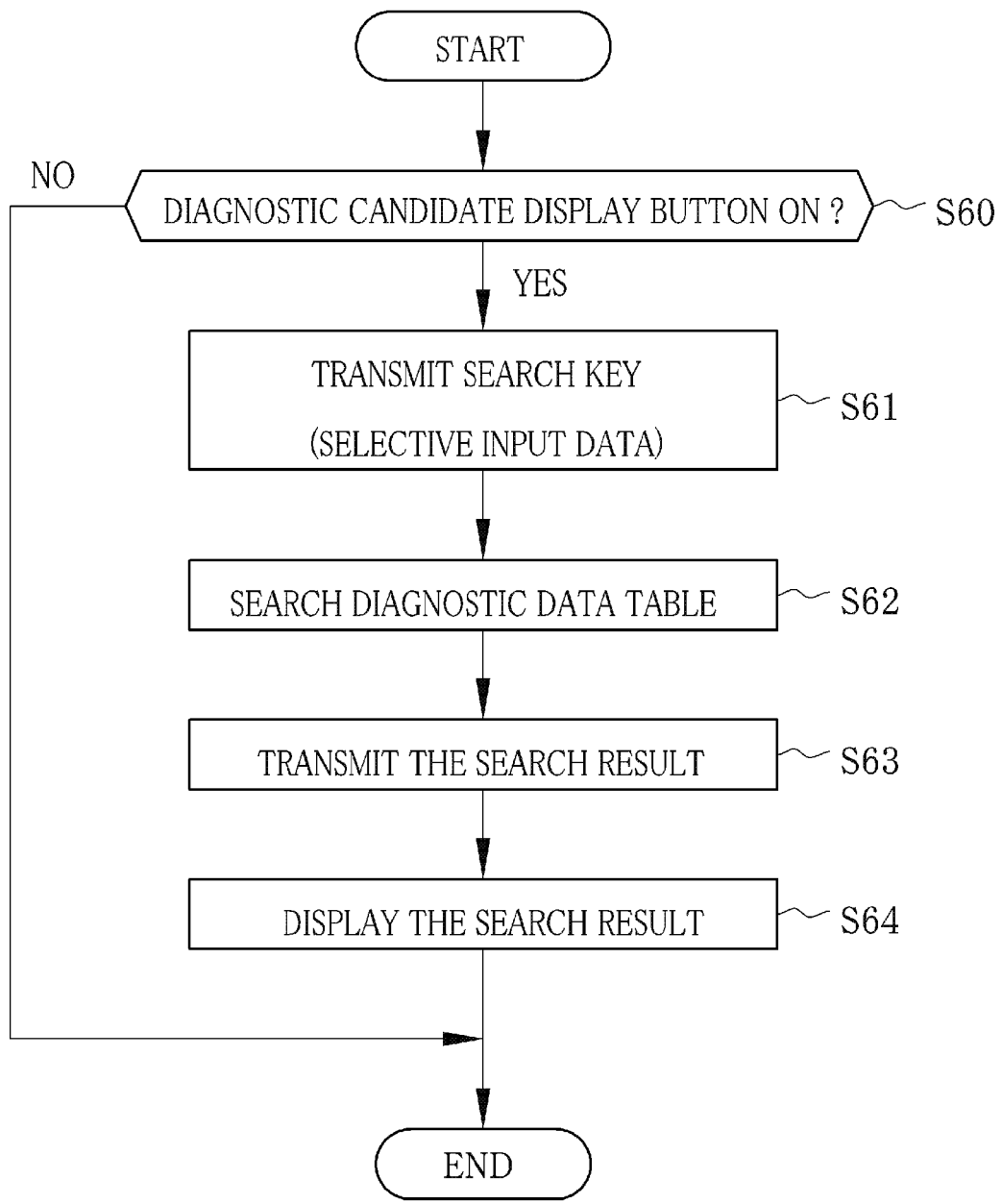
FIG. 31 is a flowchart illustrating a sequence of retrieving diagnostic candidates from the diagnostic data table.

Referring to FIG. 31, when the diagnostic candidate display button 96 is operated during the report creation process ("yes" in step S60), the console controller 40 sends the present state of selective data entry as the search key to the database access controller 41. The database access controller 41 sends a search request with the search key for searching diagnostic candidates to the search processor 72 of the database server 14 (step S61).

Then the search processor 72 searches the diagnostic data table 94 for data of those diagnostic names which have been registered in under the corresponding state of selective data entry to the search key (step S62), and sends the extracted data as a search result back to the database access controller 41 (step S63).

The database access controller 41 transfers the search result to the console controller 40, so that the console controller 40 controls the monitor 37b to pop up the diagnostic candidate display window 98 on the basis of the search result (step S64).

As described so far, since the data of diagnosis, including the name of disease and the certainty on the diagnosis, are stored and managed in association with the selective input data, such as entered by selecting the term selection buttons 51, the medical information system 90 can retrieve some diagnostic names from the stored data according to the selective input data, to suggest them as candidates in response to a search request for inferred diseases. This method is superior in accuracy to the prior arts where the diagnostic candidates are inferred from such phrases and terms that are extracted from a comment on findings through character recognition.

Serving the selective input data as the search key ensures extraction or retrieval of those diagnostic names as candidates which can be inferred from the corresponding state of selective data entry. Accordingly, the extracted diagnostic names are doubtlessly adequate and reliable, and the doctor in charge of creating a report 18 can make an exact diagnosis with reference to these diagnostic candidates.

In addition to the selective input data, the degree of certainty may serve as a search key for extracting diagnostic candidates from the data accumulated in the diagnostic data table 94. For example, when the diagnostic candidate display button 96 is clicked on after the degree of certainty is selected on the pull-down menu 75, the selected certainty degree may be included in the search key. Alternatively, independently of the pull-down menu 75, a GUI may be provided for designating the degree of certainty as a search key for diagnostic names, e.g. "all ranks", "the ranks of suspected and exception", etc. In that case, the search processor 72 extracts those diagnostic names as candidates which are stored in the group of the designated degree(s) of certainty under the designated state of selective data entry. Thus the extracted diagnostic names of the designated degree of certainty are displayed on a diagnostic candidate display window 98.

Instead of displaying the diagnostic candidate display window 98 in response to the diagnostic candidate display button 96, it is possible to configure the system to display the diagnostic candidate display window 98 automatically, for example, when the selection on the term selection buttons 51 and the data input in the data entry boxes 61 are complete, or designated data items are input through the term selection buttons 51 and/or the data entry boxes 61. However, the automatic display of diagnostic candidates may be unnecessary or cumbersome for some doctors. Therefore, it is preferable to provide a button or the like for displaying diagnostic candidates only when needed like in the above embodiment.

In the early period of installation of the medical information system 90 in practice, the number of reports 18 accumulated in the report database 21 can be insufficient for providing a practical diagnostic data table 94 that is useful for inferring and displaying adequate diagnostic candidates. To solve this problem, a default diagnostic data table 94 containing diagnostic data collected from a certain number of past medical reports may be previously provided in the diagnosis database 92. Alternatively, the diagnostic candidate display button 96 may be so designed that it will get active first when a sufficient number of cases are accumulated in the diagnostic data table 94.

It is also possible to use the doctor ID for managing the diagnostic data table 94 in relation to the individual radiological doctors. Thereby, diagnostic names may be nominated as candidates from among those diagnoses which have been made by a designated doctor. The doctor ID may be entered for user authentication to login the report creation terminal 13.

In the above embodiment, the number of times a diagnosis has been given under a certain condition represented by the selective input data, and its percentage to the total number of diagnoses given under this condition are registered in combination with that diagnostic name, so that diagnostic candidates may be inferred and displayed according to the registered number of times and its percentage. Instead of or in addition to these factors, likelihood may be adopted as an index for determining the candidates.

Namely, likelihood of a diagnosis X represents a probability of making the diagnosis X under a certain condition A, and the following formulas may be given according to the Baye's theorem, provided that P(X|A) is posttest probability of a diagnosis X, P(A|X) is likelihood, and P(X) is pretest probability:

$$P(X|A) \propto P(A|X) * P(X)$$

$$P(A|X) = Nxa/Nx$$

wherein Nx represents the total number of times the diagnosis X have been given, and Nxa the number of times the diagnosis X have been given under the condition A.

The likelihood calculated with the above formulas may be stored in association with the diagnostic name and the corresponding state of selective data entry in the form of a likelihood table 106 as shown in FIG. 32.

In general, hepatocarcinoma account for about 90% of all cases of liver cancers, while hepatoblastoma constitutes only a few percent. For instance, when the number of patients with hepatocarcinoma is 200 and the number of patients with hepatoblastoma is five as a result of past examinations, but the number of patients diagnosed as hepatocarcinoma is 20 and the number of patients diagnosed as hepatoblastoma is 2 under a particular condition or state of selective data entry A, the ratio of the posttest probability of hepatoblastoma to hepatocarcinoma is 2/20 with regard to the condition A. In view of the numbers of times the respective diagnoses have been made, the probability of hepatoblastoma is merely 1/10 of hepatocarcinoma in this condition A. As a result, hepatoblastoma will be regarded as an exceptional or rare case to be diagnosed in this condition A. However, in view of the likelihood in the condition A, hepatocarcinoma is 20/200=0.1, whereas hepatoblastoma is 2/5=0.4. Therefore, the likelihood of diagnosing as hepatoblastoma is higher than that of hepatocarcinoma in this condition A.

Consequently, some disease may have a higher likelihood in a certain condition or state of selective data entry even while this disease is a rare case with respect to the number of all diagnoses. In contrast, even a popular disease that have been diagnosed to many patient can have a lower likelihood if the likelihood is calculated taking account of the selective input data in the medical reports and the probability of making diagnosis of this disease is generally high regardless of the selective input data. Accordingly, selecting diagnostic candidates depending upon the likelihood will provide more adequate and reliable candidates inferable from the state of selective data entry, in comparison with the case where diagnostic candidates are selected depending upon the frequency or percentage of entry of each diagnostic name to the total number of entries of diagnostic names. Thus, using the likelihood as an index for diagnosis may make doctors notice of such rare cases that the doctors tend to look over as diagnostic candidates.

In the embodiment using the likelihood table 106, the search processor 72 extracts some diagnostic names as candidates from the diagnosis data table 94 in the same manner as described above and thereafter refers to the likelihood of the extracted diagnostic names from the likelihood table 106. Then the search processor 72 sends the likelihood together with the extracted diagnostic candidates to the database access controller 41.

The diagnostic candidates may be displayed in order of most likely. In the case where the likelihood is adopted in addition to the number of times of entries and its percentage, it is desirable to provide a GUI for designating the priority among these factors before executing the search process. It is also preferable to display the number of times of entries and the likelihood along with the individual diagnostic candidates and highlight maximum values, like as shown in a diagnostic candidate display window 108 of FIG. 33.

In a modified embodiment, data representative of benign-malignant relation between respective diagnostic names a maybe stored in another table in the diagnosis database 92. When a past medical report is copied for use in creating a present medical report, the benign-malignant relation of an extracted diagnostic name to a diagnostic name described in the past medical report may be retrieved and displayed with the extracted diagnostic name. For example, in case where the extracted diagnostic name is "malignant tumor" and the diagnostic name described in the corresponding past report is "benignant tumor", the doctor may determine that the lesion in question gets worse. Thus, the data of benign-malignant relation may be utilized for judging therapeutic efficacy from the follow-up examination.

In the above embodiments, only one diagnostic name is selectable or written in the diagnosis input area 74. It is possible to provide an add button or the like to enable inputting another diagnostic name at a different certainty degree. The diagnostic candidate display window may be configured to permit checking more than one check box to select more than one diagnostic name as candidates. In that case, one or more additional diagnostic name entry boxes 76 may automatically be provided in the diagnosis input area 74 each in combination with an additional certainty degree entry box.

In the above embodiment, a doctor in charge of radiographic interpretation may refer to diagnostic candidates on the report creation terminal 13. It is of course possible that a requesting doctor of the diagnostic and treatment department 12 who has requested a report 18 may refer to diagnostic candidates while reading the report 18. In that case, an entry box for inputting one or more search keys for diagnostic candidates should be provided on a screen of the terminal 11. Then the database server 14 may send back some diagnostic candidates as the search result. It is also possible to forward the diagnostic candidates to the requesting doctor automatically along with the complete report 18. Then the requesting doctor can refer to the diagnostic candidates in order to certify the authenticity of the diagnosis written in the report 18 or change the diagnosis if necessary.

Although the above described embodiments use the keyboard and the mouse as the input devices, the input devices may include other devices such as a microphone. In that case, the term selection buttons 53 may be selectable through voice commands.

Medical examinations executable in the medical information system of the present invention are not limited to radiological examinations but may include any kinds of examinations including position emission tomography (RET), endoscopy, etc. The present invention is not only applicable to reports on radiographic interpretation of examination images 18 but also applicable to other kinds of medical reports based on other kinds of examination than radiography, e.g. numerical data obtained through pathological examinations, laboratory tests, sample examination, or physiological tests, and waveform diagrams like electrocardiograms. The report may contain multiple comments based on various data obtained through different kinds of examinations.

Although a single report creation terminal is illustrated in the above embodiments, the medical information system of the present invention may include multiple report creation terminals. Moreover, the rendering data may be stored in the database server instead of the storage device. In that case, the database access controller sends a request for retrieving the rendering data from the database server.

Although the function of the console controller and the functions of the storage processor and the search processor are divided into the report creation terminal and the database server in the above embodiment, these functions may be integrated into a specific apparatus. Then the specific apparatus may provide the course information on a designated lesion from the lesion database or data of diagnostic candidates from the diagnosis database.

In the case where the medical information system is of a client-server type that consists of clients (report creation terminals) and a server (database server), like in the above embodiments, the client program for editing the reports may be a specific program or a general-use browser compatible to WWW (World Wide Web) protocols such as HTTP (Hypertext Transfer Protocol) may be applicable.

In the case of specific program, a report editing screen will be produced based on screen data defined by the specific program. In the case of general-use browser, data of a report editing screen may be stored in a Web server, so that the client may download the screen data as processed into a Web page format from the Web server. The client browser compiles the source code of the downloaded Web page to produce the report editing screen. The database server may double as the web server, or the web server may be provided separately from the database server. In the case of general-use browser, a CPU of the Web server may constitute the editorial processor, the console controller and other functional components in cooperation with or independently of the CPU of the client.

The above-described databases maybe stored in other devices than the database server. For example, a network attached storage (NAS) or a storage device connectable through a network such as a storage area network (SAN) maybe used for storing the databases. The physical structure of the medical information system of the invention may therefore be modified appropriately.

In the above embodiment, the terminals and the database server are connected to each other through a local area network. Where the terminals of the system are installed in a wide area, they may be connected through a combination of a wide area network and local area networks.

It should be appreciated that the present invention may be embodied as a software program or a storage medium containing the software program. Therefore, such a program or storage medium should be considered to be within the scope of the present invention.

It should be understood that the embodiments of the present invention have been disclosed for illustrative purposes only. Those skilled in the art will appreciate that various modifications, additions and substitutions are possible without departing from the scope and spirit of the invention as disclosed in the accompanying claims.

What is claimed is:

1. A medical information providing apparatus comprising:
 a storage device for storing selective input data on a lesion in a database in association with a lesion ID given to each individual lesion, the selective input data being entered through a template for selectively inputting at least some words and phrases which constitute a comment on the lesion;
 a search device for searching said database for data of past medical reports relating to a desired lesion in response to a search request, and extracting course information presenting a change over time of the desired lesion from the data of said past medical reports; and
 a display control device for displaying the course information on the desired lesion, wherein, said search device retrieves selective input data of a past medical report relating to the lesion to be described in a present medical report, said display control device displays, on the basis of the retrieved selective input data, a copied template that reproduces a same condition of selective input on a template used on creating said past medical report such that a new set of selective input data on the same lesion may be input through the copied template in the present medical report, and said storage device stores the new set of selective input data entered through the copied template in association with the same lesion ID as associated with the selective input data of said past medical report, or said storage device issues a new lesion ID to store the selective input data of the present medical report in association with the new lesion ID when said database does not contain any selective input data that relate to the same lesion as described in the present medical report.

2. The medical information providing apparatus as recited in claim 1, wherein a new template or a template copying a condition of selective input in a presently displayed template may be added to a medical report editing screen, or a new description area may be added to the presently displayed template, in order to describe different lesions.

3. The medical information providing apparatus as recited in claim 1, wherein said search device uses the lesion ID as a search key and extracts the course information on a lesion identified with said lesion ID.

4. The medical information providing apparatus as recited in claim 1, wherein said search device uses selective input data entered through a presently displayed template as a search key and extracts the course information on lesions associated with identical or similar selective input data to the search key.

5. The medical information providing apparatus as recited in claim 1, wherein the course information include at least one of images containing the lesion, the onset site of the lesion, numerical values indicating the size of the lesion, information about whether the lesion gets better or worse, the diagnostic name of the lesion, and the illness stage.

6. The medical information providing apparatus as recited in claim 1, wherein said display control device lists the course information to display.

7. The medical information providing apparatus as recited in claim 1, wherein when said search device extracts the course information on a plurality of cases, said display control device comparably displays the course information of the plurality of cases.

8. The medical information providing apparatus as recited in claim 1, wherein when the extracted course information includes numerical values, said display control device displays the course information in a graph plotting the numerical values along a time axis.

9. The medical information providing apparatus as recited in claim 1, wherein said storage device stores the selective input data in association with the lesion ID while sorting the selective input data by patients.

10. The medical information providing apparatus as recited in claim 1, wherein said storage device and said search device are composed in a server having said database, and said display control device is composed in a client terminal that is connected to said server over a network, and wherein said server and said client terminal exchange the search request to said search device and the course information extracted from said database through the network.

11. A medical information providing method comprising the steps of:

storing selective input data on a lesion in a database in association with a lesion ID given to each individual lesion, the selective input data being entered through a template for selectively inputting at least some words and phrases which constitute a comment on the lesion;

searching said database for data of past medical reports relating to a desired lesion in response to a search request;

extracting course information presenting a change over time of the desired lesion from the data of said past medical reports; and displaying the course information on the desired lesion, wherein, a search device for the step of searching said database retrieves selective input data of a past medical report relating to the lesion to be described in a present medical report, a display control device for the step of displaying the course information displays, on the basis of the retrieved selective input data, a copied template that reproduces a same condition of selective input on a template used on creating said past medical report such that a new set of selective input data on the same lesion may be input through the copied template in the present medical report, and a storage device for the step of storing the selective input data stores the new set of selective input data entered through the copied template in association with the same lesion ID as associated with the selective input data of said past medical report, or said step of storing issues a new lesion ID to store the selective input data of the present medical report in association with the new lesion ID when said database does not contain any selective input data that relate to the same lesion as described in the present medical report.

12. A computer program product stored on a non-transitory computer-readable medium for providing medical information, said program causing a computer to perform the functions of:

storing selective input data on a lesion in a database in association with a lesion ID given to each individual lesion, the selective input data being entered through a template for selectively inputting at least some words and phrases which constitute a comment on the lesion;

searching said database for data of past medical reports relating to a desired lesion in response to a search request;

extracting course information presenting a change over time of the desired lesion from the data of said past medical reports; and displaying the course information on the desired lesion, wherein, a search device for the step of searching said database retrieves selective input data of a past medical report relating to the lesion to be described in a present medical report, a display control device for the step of displaying the course information displays, on the basis of the retrieved selective input data, a copied template that reproduces a same condition of selective input on a template used on creating said past medical report such that a new set of selective input data on the same lesion may be input through the copied template in the present medical report, and a storage device for the step of storing the selective input data stores the new set of selective input data entered through the copied template in association with the same lesion ID as associated with the selective input data of said past medical report, or said step of storing issues a new lesion ID to store the selective input data of the present medical report in association with the new lesion ID when said database does not contain any selective input data that relate to the same lesion as described in the present medical report.

13. A medical information providing apparatus comprising:
    a first display control device for displaying a medical report editing screen having a selective data input area for selectively inputting at least some words and phrases which constitute a comment on findings and a diagnosis input area;
    a storage device for storing selective input data entered through the selective data input area in a first database in association with a diagnostic name entered through the diagnosis input area;
    a search device for searching the first database in response to a search request that provides the entered selective input data as a search key, to extract diagnostic names which are association with identical or similar selective input data to the search key; and
    a second display control device for displaying the extracted diagnostic names, wherein,
    said storage device registers the number of times each individual diagnostic name has been input in the first database, and when the diagnostic name to be stored in association with a set of selective input data has already been stored in association with an identical or similar set of selective input data, said storage device increments the number of times the diagnostic name has been input, and when not, said storage device creates a new area in the first database for registering the diagnostic name and the number of times the diagnostic name has been input,
    said search device extracts along with each diagnostic name at least one of the number of input times of the diagnostic name and the percentage of the number of input times of the diagnostic name to the total number of input times, and
    said display control device displays extracted diagnostic names according to the number of inputs or the percentage.

14. The medical information providing apparatus as recited in claim 13, wherein
    said diagnosis input area is provided with a graphical user interface for selectively inputting the degree of certainty on the diagnostic name, and wherein
    said storage device sorts the diagnostic names by the selected degrees of certainty in the first database; and
    said second display control device displays the diagnostic names in order of certainty.

15. The medical information providing apparatus as recited in claim 13, further comprising a second database that stores diagnostic names, each in association with at least a set of selective input data and likelihood of inferring the diagnostic name from the associated set of selective input data, wherein
    said search device may extract at least a diagnostic name based on the search key and may also extract the likelihood of inferring the extracted diagnostic name from the selective input data that are identical or similar to the search key; and
    said display control device may display the extracted diagnostic name along with the likelihood.

16. The medical information providing apparatus as recited in claim 13, further comprising a third database storing data representative of benign-malignant relation between respective diagnostic names, wherein
    said search device extracts the benign-malignant relation of an extracted diagnostic name to a diagnostic name described in a past medical report which is copied for use in creating a present medical report; and
    said display control device displays the benign-malignant relation with the extracted diagnostic names.

17. The medical information providing apparatus as recited in claim 13, wherein
    said storage device and said search device are composed in a server having said database, and said display control device is composed in a client terminal that is connected to said server over a network, and wherein
    said server and said client terminal exchange the search request to said search device and the course information extracted from said database through the network.

18. A medical information providing method comprising the steps of:
    displaying a medical report editing screen having a selective data input area for selectively inputting at least some words and phrases which constitute a comment on findings and a diagnosis input area;
    storing selective input data entered through the selective data input area in a first database in association with a diagnostic name entered through the diagnosis input area;
    searching the first database in response to a search request that provides the entered selective input data as a search key, to extract diagnostic names which are association with identical or similar selective input data to the search key; and
    displaying the extracted diagnostic names, wherein,
    a storage device for the step of storing the selective input data registers the number of times each individual diagnostic name has been input in the first database, and when the diagnostic name to be stored in association with a set of selective input data has already been stored in association with an identical or similar set of selective input data, said storage device increments the number of times the diagnostic name has been input, and when not, said storage device creates a new area in the first database for registering the diagnostic name and the number of times the diagnostic name has been input,
    a search device for the step of searching the first database extracts along with each diagnostic name at least one of the number of input times of the diagnostic name and the percentage of the number of input times of the diagnostic name to the total number of input times, and
    a display control device for the step of displaying the medical report editing screen displays extracted diagnostic names according to the number of inputs or the percentage.

19. A computer program product stored on a non-transitory computer-readable medium for providing medical information, said program causing a computer to perform the functions of:
    displaying a medical report editing screen having a selective data input area for selectively inputting at least some words and phrases which constitute a comment on findings and a diagnosis input area;
    storing selective input data entered through the selective data input area in a first database in association with a diagnostic name entered through the diagnosis input area;

searching the first database in response to a search request that provides the entered selective input data as a search key, to extract diagnostic names which are association with identical or similar selective input data to the search key; and displaying the extracted diagnostic names, wherein, a storage device for the step of storing the selective input data registers the number of times each individual diagnostic name has been input in the first database, and when the diagnostic name to be stored in association with a set of selective input data has already been stored in association with an identical or similar set of selective input data, said storage device increments the number of times the diagnostic name has been input, and when not, said storage device creates a new area in the first database for registering the diagnostic name and the number of times the diagnostic name has been input, a search device for the step of searching the first database extracts along with each diagnostic name at least one of the number of input times of the diagnostic name and the percentage of the number of input times of the diagnostic name to the total number of input times, and a display control device for the step of displaying the medical report editing screen displays extracted diagnostic names according to the number of inputs or the percentage.

* * * * *